(12) United States Patent
Kief et al.

(10) Patent No.: US 11,832,817 B2
(45) Date of Patent: Dec. 5, 2023

(54) STAPLE LINE SURGICAL BUTTRESS

(71) Applicant: Lexington Medical, Inc., Bedford, MA (US)

(72) Inventors: Jameson Kief, Wakefield, MA (US); Andrew Marecki, Wilbraham, MA (US)

(73) Assignee: Lexington Medical, Inc., Bedford, MA (US)

( * ) Notice: Subject to any disclaimer, the term of this patent is extended or adjusted under 35 U.S.C. 154(b) by 0 days.

(21) Appl. No.: 17/902,504

(22) Filed: Sep. 2, 2022

(65) Prior Publication Data

US 2023/0072192 A1 Mar. 9, 2023

Related U.S. Application Data

(60) Provisional application No. 63/240,572, filed on Sep. 3, 2021.

(51) Int. Cl.
| | | |
|---|---|---|
| *A61B 17/064* | (2006.01) | |
| *A61B 17/072* | (2006.01) | |
| *A61B 17/00* | (2006.01) | |

(52) U.S. Cl.
CPC .............. *A61B 17/07292* (2013.01); *A61B 2017/00004* (2013.01); *A61B 2017/07257* (2013.01); *A61B 2017/07271* (2013.01)

(58) Field of Classification Search
CPC ...... A61B 17/07292; A61B 2017/0004; A61B 2017/0406
See application file for complete search history.

(56) References Cited

U.S. PATENT DOCUMENTS

| | | |
|---|---|---|
| 5,503,638 A | 4/1996 | Cooper et al. |
| 5,902,312 A | 5/1999 | Frater |
| 6,503,257 B2 | 1/2003 | Grant et al. |
| 6,592,597 B2 | 7/2003 | Grant et al. |
| 6,656,193 B2 | 12/2003 | Grant et al. |
| 7,147,138 B2 | 12/2006 | Shelton |
| 7,547,312 B2 | 6/2009 | Bauman et al. |
| 7,845,533 B2 | 12/2010 | Marczyk et al. |
| 7,950,561 B2 | 5/2011 | Aranyi |
| 8,011,555 B2 | 9/2011 | Tarinelli et al. |
| 8,028,883 B2 | 10/2011 | Stopek |
| 8,157,149 B2 | 4/2012 | Olson et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,408,440 B2 | 4/2013 | Olson et al. |
| 8,453,910 B2 | 6/2013 | Bettuchi et al. |
| 8,479,968 B2 | 7/2013 | Hodgkinson et al. |
| 8,584,920 B2 | 11/2013 | Hodgkinson |
| 8,631,989 B2 | 1/2014 | Aranyi et al. |
| 8,899,464 B2 | 12/2014 | Hueil et al. |

(Continued)

*Primary Examiner* — Eyamindae C Jallow
(74) *Attorney, Agent, or Firm* — Brooks, Cameron & Huebsch, PLLC

(57) ABSTRACT

The present disclosure includes a surgical buttress or reinforcement for a surgical stapler assembly. The surgical stapler includes an anvil with a tissue contacting surface and a staple cartridge with a tissue contacting surface. The surgical buttress, in either one or two pieces, is releasably secured to the tissue contacting surfaces. The staples are delivered through the surgical buttress to provide a reinforcement for the staples.

20 Claims, 24 Drawing Sheets

(56) References Cited

U.S. PATENT DOCUMENTS

| | | |
|---|---|---|
| 9,010,606 B2 | 4/2015 | Aranyi et al. |
| 9,084,602 B2 | 7/2015 | Gleiman |
| 9,101,359 B2 | 8/2015 | Smith et al. |
| 9,192,378 B2 | 11/2015 | Aranyi et al. |
| 9,277,922 B2 | 3/2016 | Carter et al. |
| 9,345,479 B2 | 5/2016 | Tarinelli et al. |
| 9,433,419 B2 * | 9/2016 | Gonzalez ......... A61B 17/00491 |
| 9,668,736 B2 | 6/2017 | Holsten et al. |
| 9,675,351 B2 | 6/2017 | Hodgkinson et al. |
| 9,693,772 B2 * | 7/2017 | Ingmanson ...... A61B 17/07292 |
| 9,974,538 B2 * | 5/2018 | Baxter, III ......... A61B 17/0644 |
| 9,999,408 B2 * | 6/2018 | Boudreaux ...... A61B 17/07207 |
| 2014/0048580 A1 | 2/2014 | Merchant et al. |
| 2016/0128694 A1 * | 5/2016 | Baxter, III ........... A61B 17/105 |
| | | 227/176.1 |
| 2016/0278765 A1 | 9/2016 | Shelton, IV et al. |
| 2017/0079653 A1 | 3/2017 | Kostrzewski |
| 2018/0250000 A1 * | 9/2018 | Hodgkinson ........ A61N 5/1007 |
| 2019/0038285 A1 * | 2/2019 | Mozdzierz ....... A61B 17/07292 |
| 2021/0259687 A1 * | 8/2021 | González et al. .......................... |
| | | A61B 17/07207 |

\* cited by examiner

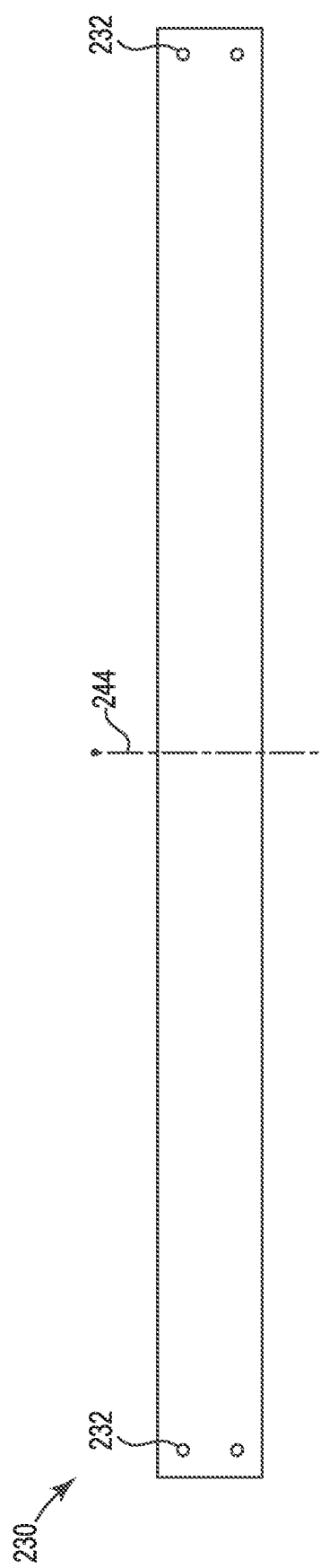
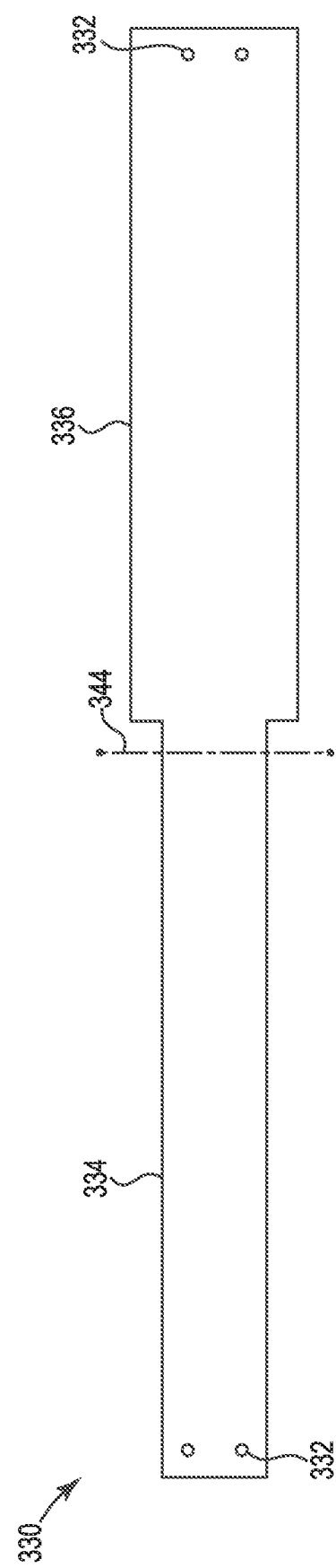

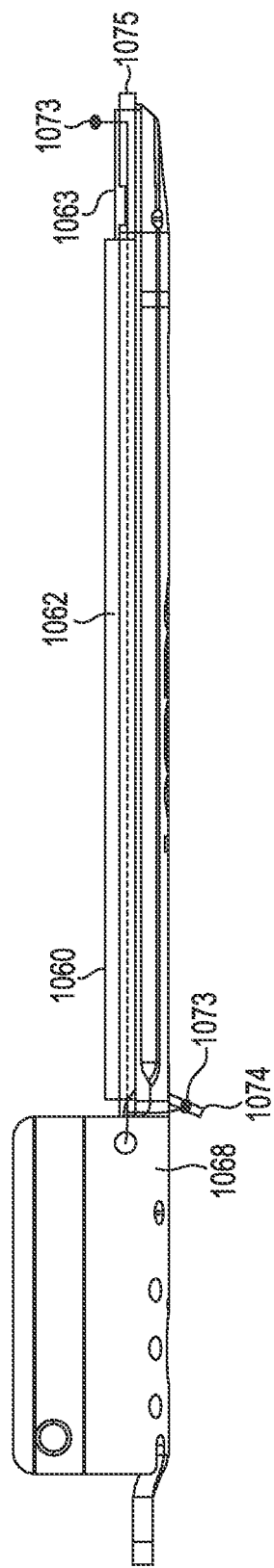

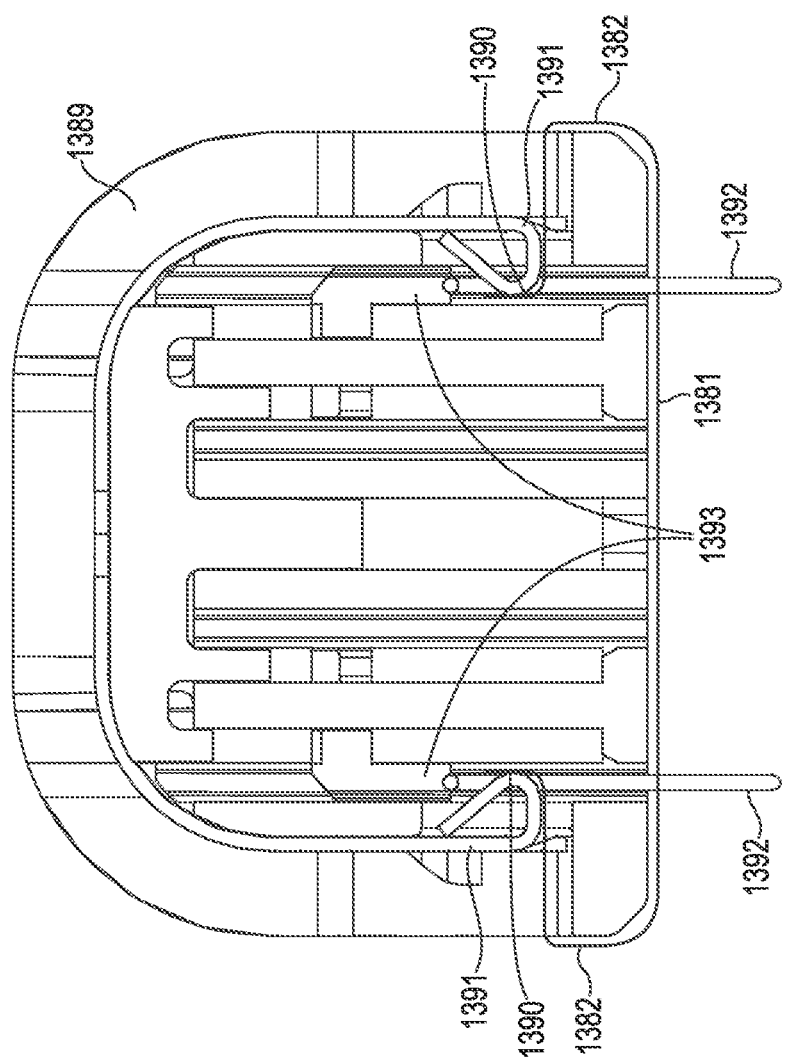

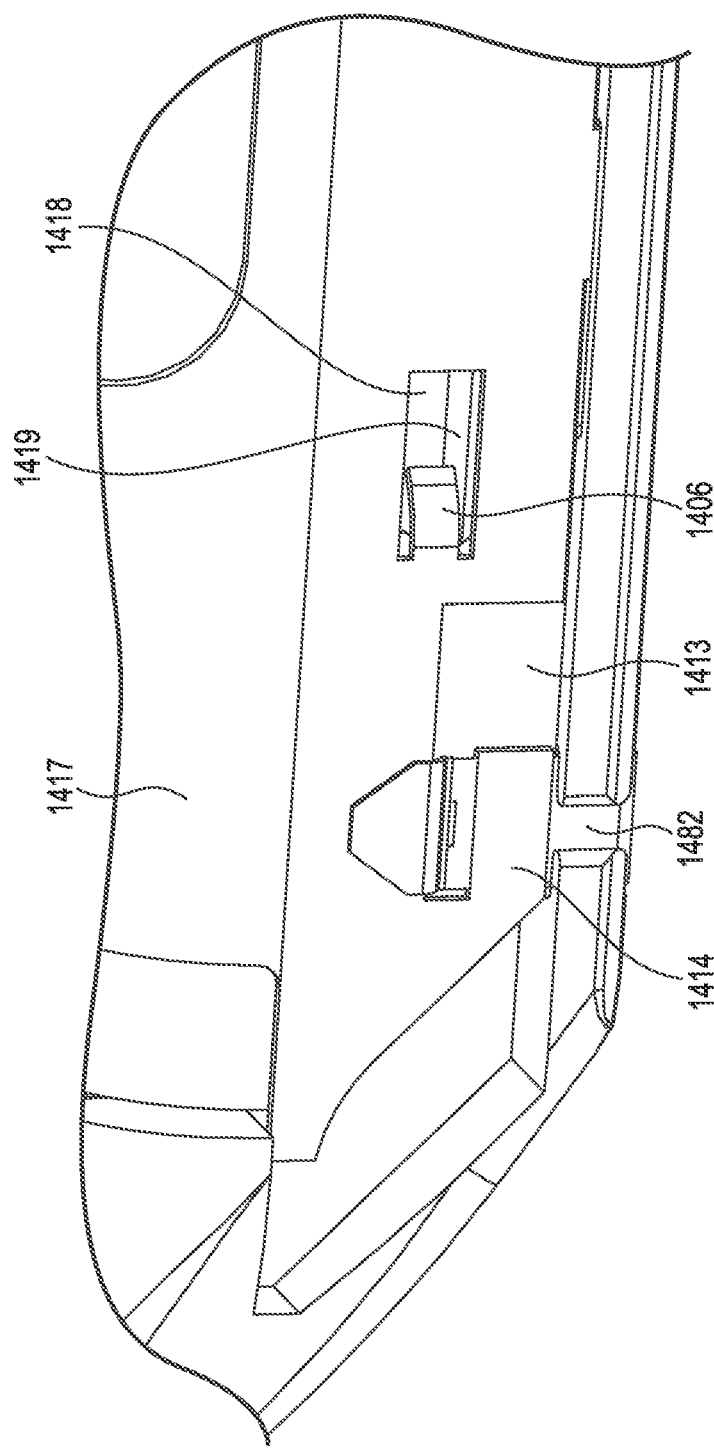

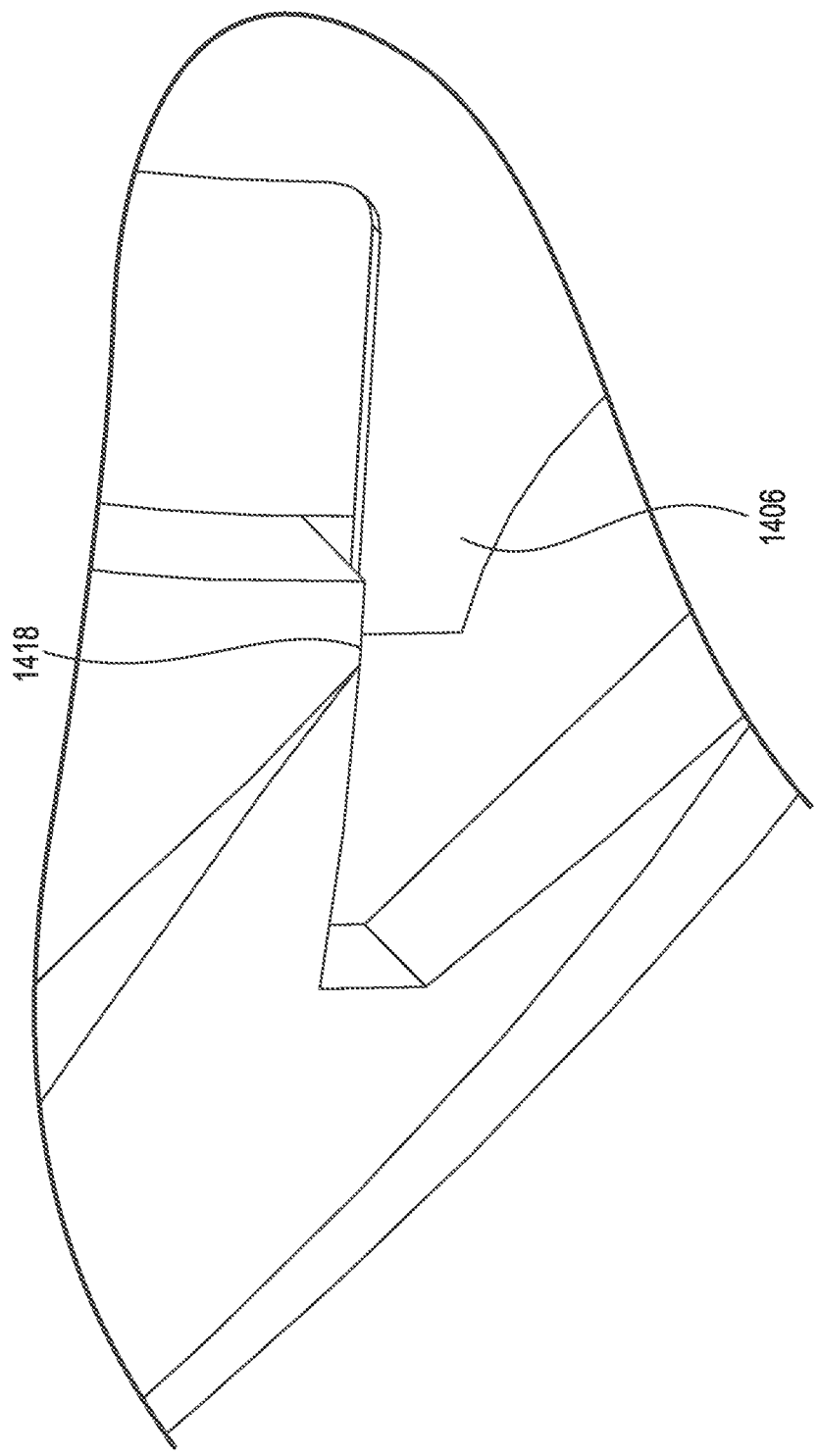

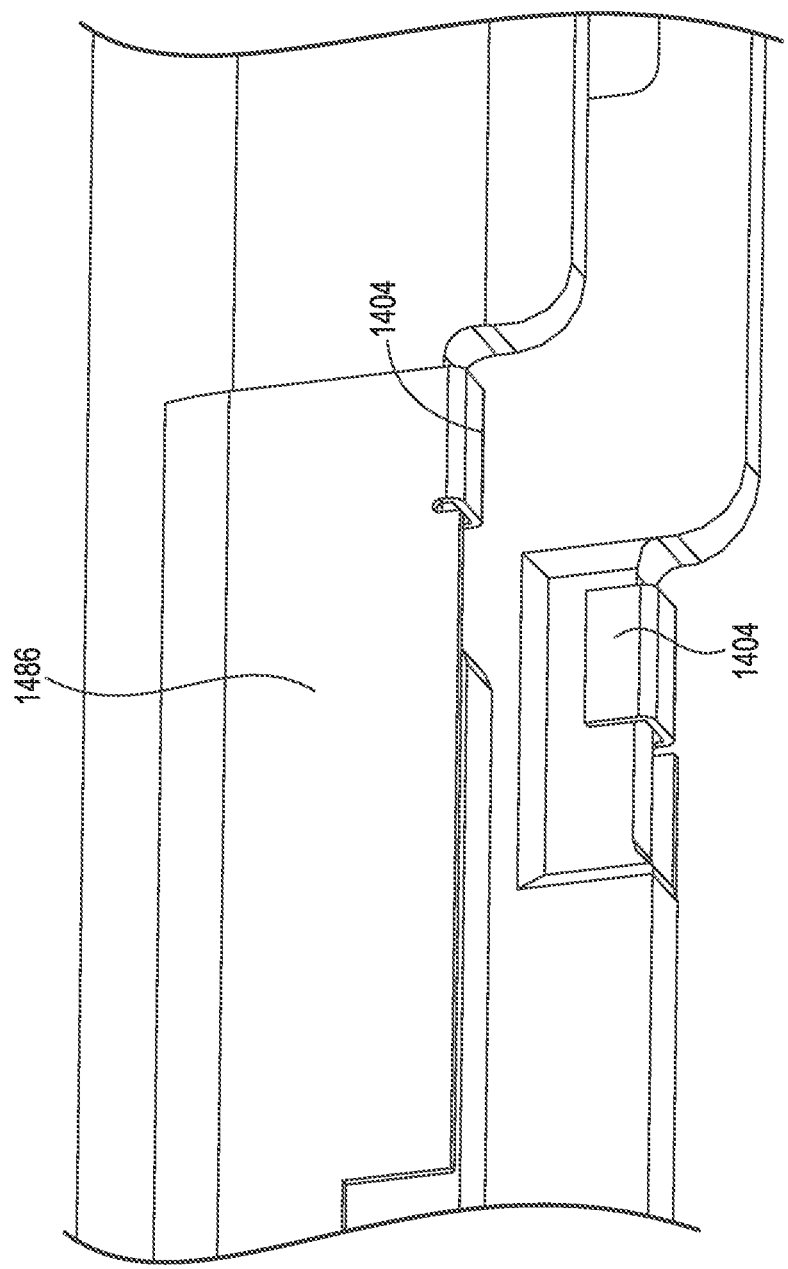

STAPLE LINE SURGICAL BUTTRESS

PRIORITY INFORMATION

This application claims benefit of U.S. Provisional Application No. 63/240,572 filed Sep. 3, 2021, the specification of which is incorporated herein by reference.

TECHNICAL FIELD

The present disclosure relates generally to surgical stapling assemblies and, more particularly, to surgical buttresses and staple line surgical reinforcements.

BACKGROUND

A surgical stapler is a fastening device used to clamp tissue between opposing jaw structures to join tissue using surgical fasteners and separate tissue using a cutting blade. Surgical staplers can include two elongated members used to clamp the tissue. One of the elongated members can include one or more reloadable cartridges and the other elongated member can include an anvil that can be used to form a staple when driven from the reloadable cartridge. A surgical stapler can receive one or more reloadable cartridges. An example of reloadable cartridges can include having rows of staples having a linear length. For example, a row of staples can have a linear length between 30 mm and 60 mm. A staple can be ejected by actuation of a movable handle member that is a part of the surgical handle assembly of the surgical stapler.

Some surgical staplers are equipped with an electric motor which can provide the power to clamp tissue, deliver staples, and provide power for other aspects of a surgical stapler.

When using a surgical stapler, it is important to effectively seal the staple line against air or fluid (such as blood) leakage. In some instances, it is desirable to reinforce the staple line to more evenly distribute the force of the staple over a larger surface and to prevent tears in the tissue or pulling of the staples through the tissue. One method of accomplishing these goals is through the placement of a biocompatible fabric reinforcing material, or a "buttress," between the staple and the underlying tissue. In this embodiment, a layer of buttress material is placed against the tissue and the tissue is stapled in conventional manner. One way to accomplish this is for the layer of buttress material to be positioned on the stapling instrument itself prior to stapling the tissue.

BRIEF DESCRIPTION OF THE DRAWINGS

FIG. 2 is a schematic diagram of a surgical buttress in accordance with a number of embodiments of the present disclosure.

FIG. 3 is a schematic diagram of a surgical buttress in accordance with a number of embodiments of the present disclosure.

FIGS. 10A, 10B, and 10C are schematic diagrams of an example of buttress material and its attachment to an anvil.

FIGS. 13A, 13B, 13C, and 13D are schematic diagrams of an example of the buttress material's attachment to a staple cartridge.

FIGS. 14A, 14B, 14C, 14D, 14E, 14F, 14G, 14H, and 14I are schematic diagrams of an example of the buttress material and its attachment to a staple cartridge.

DETAILED DESCRIPTION

Figure 1:
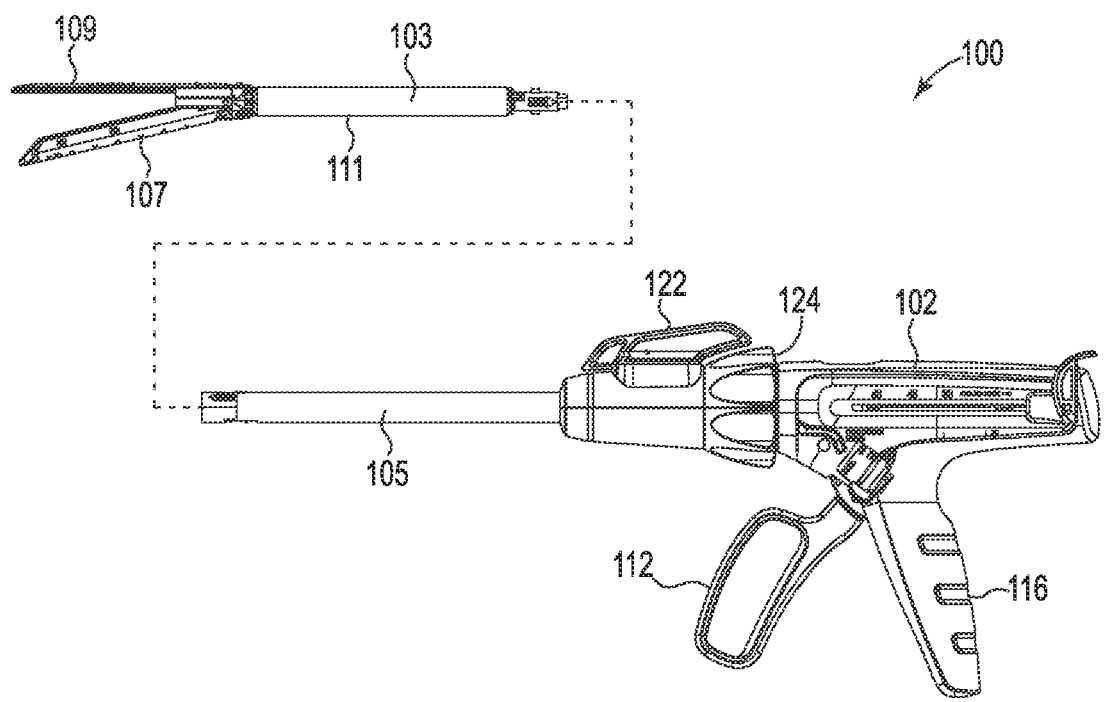
FIG. 1 is a schematic diagram of an apparatus including a surgical handle assembly and a reloadable cartridge assembly in accordance with a number of embodiments of the present disclosure.

The present disclosure includes apparatuses for buttressing and/or reinforcing a staple line for a surgical stapler assembly. An example apparatus includes a reloadable cartridge assembly and a surgical handle assembly. The surgical handle includes a movable handle that allows for the clamping (e.g., grasping) and unclamping (e.g., ungrasping) of a reloadable cartridge assembly prior to delivering staples. The reloadable cartridge assembly includes an anvil and a staple cartridge assembly, with a piece of biocompatible material mounted on and releasably secured to the anvil and/or the staple cartridge.

In a number of embodiments, the reloadable cartridge assembly can include a first elongated member and a second elongated member. The first elongated member and the second elongated member can sometimes be referred to as jaws and are part of the jaw assembly. The jaws can be used to clamp and/or grasp tissue. One of the elongated members can house one or more staple cartridges as part of a staple cartridge assembly. The other elongated member can have an anvil that can be used to form a staple when driven from the staple cartridge. In a number of embodiments, a biocompatible fabric is mounted on the anvil and staple cartridge. The biocompatible fabric can be biostable and/or bioabsorbable. In a number of embodiments, separate pieces of buttress or biocompatible fabric are mounted separately on the anvil and the staple cartridge. In some embodiments, the movement of an I-beam within an anvil will release the anvil buttress from the anvil. In a number of embodiments, the movement of an I-beam within a staple cartridge will release the cartridge buttress from the staple cartridge. In a number of embodiments, the movement of an I-beam within the staple cartridge causes a moveable cover to move and release the cartridge buttress from the staple cartridge. In some embodiments, a physician/user of a surgical stapler can manually move the cover to release the cartridge buttress from the staple cartridge.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

It is to be understood that the terminology used herein is for the purpose of describing particular embodiments only and is not intended to be limiting. As used herein, the singular forms "a", "an", and "the" can include both singular and plural referents, unless the context clearly dictates otherwise. In addition, "a number of", "at least one", and "one or more" (e.g., a number of bosses) can refer to one or more bosses, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the movable handle member, as appropriate to the context.

The figures herein follow a numbering convention in which the first digit or digits correspond to the figure number and the remaining digits identify an element or component in the figure. Similar elements or components between different figures may be identified by the use of similar digits. For example, 102 may reference element "2" in FIG. 1, and a similar element may be referenced as 202 in FIG. 2. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a schematic diagram of an apparatus 100 including a surgical handle assembly 102 and a reloadable cartridge assembly 103 in accordance with a number of embodiments of the present disclosure. The reloadable cartridge assembly 103, e.g., a disposable loading unit, can be releasably secured to a distal end of an elongated body 105 of the surgical handle assembly 102. In this example, the reloadable cartridge assembly 103 can include a cartridge shaft 111, a first elongated member 107 and a second elongated member 109 that are pivotably attached and that can be used to clamp tissue. One of the elongated members can house one or more staple cartridges. The other elongated member can have an anvil that can be used to form a staple when driven from the staple cartridge. Apparatus 100 can receive reloadable cartridge assemblies having rows of staples. In a number of embodiments, third party reloadable cartridge and/or reloadable cartridge assemblies may be used with the surgical handle assembly 102 and embodiments of surgical handle assembly 102 may be configured to receive the same.

The surgical handle assembly 102 of FIG. 1 may include a radial positioner 124, an articulation assembly activated by articulation knob 122, and non-movable or stationary handle 116. The reloadable cartridge assembly 103 can be actuated using articulation knob 122 and/or radial positioner 124 to reach a stapling site. Radial positioner 124 rotates the reloadable cartridge assembly. Knob 122 positions the elongated members 107 and 109 at a particular angle for sta-pling. The knob 122 can be configured to actuate rotationally and the reloadable cartridge assembly 103 can rotate about an axis of a particular plane in response to the knob 122 being actuated rotationally by a user. Movable clamping handle 112 can be used to clamp and unclamp elongated members 107 and 109.

In FIG. 1, after movable handle 112 has been used to clamp elongate members 107 and 109, further activation of handle 112 will cause a gear rack to move distally to effect the delivery of staples. In some embodiments, an I-beam is used to deliver the staples. As a drive shaft is moved distally, the I-beam is pushed through the anvil and staple cartridge to drive the staples out of the staple cartridge and into the anvil which is used to shape the staples. The distal end of the I-Beam includes a cutting edge that cuts the stapled tissue and the surgical buttress.

While FIG. 1 shows a manually operated handle assembly, the inventions herein are equally applicable to a motor driven handle. In a motor driven handle assemble, a power trigger can be used to activate the electric motor to effect the delivery of staples. A safety switch may be used to allow power to flow to the electric motor and/or block the power trigger from being activated. A reverse (e.g., retract) button can be used to activate the electric motor to move the gear rack proximally.

Figure 4:
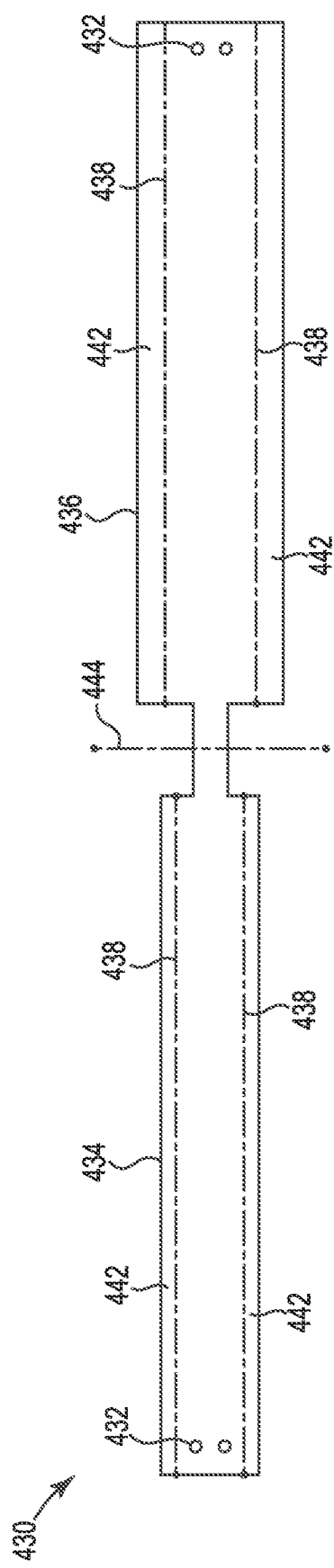
FIG. 4 is a schematic diagram of a surgical buttress in accordance with a number of embodiments of the present disclosure.

FIGS. 2, 3, and 4 are schematic diagrams of an example of the surgical buttress material of the invention. FIG. 2 shows an example of surgical buttress 230. In this example, the surgical buttress has a generally rectangular shape. As will be discussed below, surgical buttress 230 is mounted on the surfaces of the elongate members such that one end extends about the length of the anvil and the other end extends about the length of the staple cartridge. Anchor points 232 are used to suture surgical buttress 230 to the distal end of elongate members 107 and 109. In order for the surgical buttress to be effective, it needs to be wide enough such that both legs of a staple are driven through the surgical buttress when used. Fold line 244 is at the approximate center of surgical buttress 230.

FIG. 3 is a schematic diagram of another embodiment of surgical buttress 330. In some surgical staplers, the staple cartridge has a surface that is slightly wider than the surface of the anvil. For surgical buttress 330 to completely cover the surface of both the anvil and the staple cartridge in this instance, staple cartridge section 336 is slightly wider than anvil section 334. Anchor points 332 are provided. Fold line 344 is at the approximate center of surgical buttress 330.

FIG. 4 is a schematic diagram of another embodiment of surgical buttress 430. For surgical buttress 430 to completely cover the surface of both the anvil and the staple cartridge in this instance, staple cartridge section 436 is slightly wider than anvil section 434. Anchor points 432 are provided. During the positioning of the stapler in the proper location, the physician/user may move handle 102 such that reloadable cartridge assembly 103 moves laterally relative to the tissue to be stapled. In some instances, this may cause either the anvil portion and/or the staple cartridge portion of the surgical buttress to be moved such that it is no longer in a position that will allow for both legs of a staple to be driven through the surgical buttress. In an attempt to prevent this, a section 442 of the surgical buttress 430 is folded over and away from the surface of the anvil and staple cartridge. Dashed lines 438 show the axial fold line. Also shown is neck region 440 which has a smaller width so that it will fit into the jaw section of the stapler. In some embodiments, folded sections 442 are folded by hand or machine. In some embodiments, folded sections 442 are heat set at an approximate 90° angle from the sections of surgical buttress that cover the anvil and staple cartridge. Fold line 444 is at the approximate center of surgical buttress 430.

Figure 5:
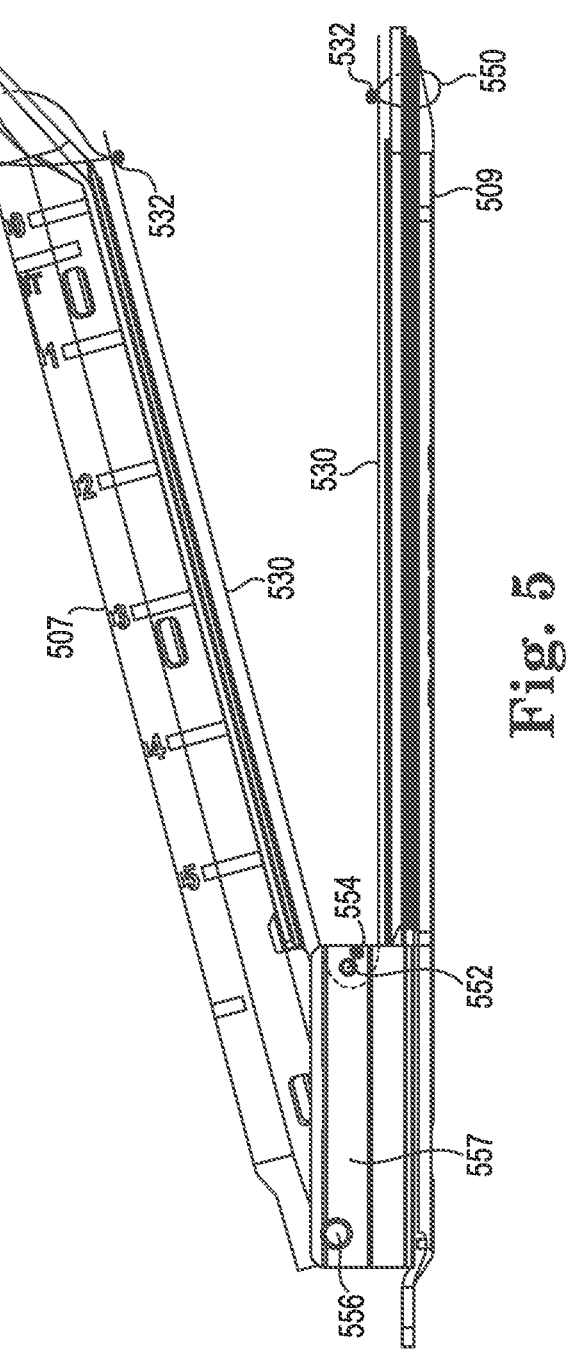
FIG. 5 is a schematic diagram of a surgical buttress releasably attached to the elongate members accordance with a number of embodiments of the present disclosure.

FIG. 5 is a schematic diagram showing an embodiment of surgical buttress 530 releasably mounted on elongate members 507 and 509. Elongate members are connected to each other at pivot point 556. In some embodiments the pivotably connected elongate members are referred to as the jaw assembly. The proximal end of one of the elongate members has side extensions 557 that extend above the surface of the elongate member with openings 552 positioned in the side extensions that is distal to pivot point 556. A distal suture loop 550 is formed at the distal end of both elongate members. A length of suture material is advanced through anchor points 532 and around one of the anvil or staple cartridges. The suture material is then tied or joined to make loop 550. This is done for both the anvil and staple cartridge. In some embodiments the suture material is not a complete loop but can be held in place by a knot positioned on the side of the surgical buttress that is opposite the surface of the anvil or staple cartridge. In this embodiment, loop 550 extends from a first side of the surgical buttress through an anchor point, around the anvil or staple cartridge, and back through the other anchor point, with a knot or other enlargement of suture material positioned at each end of the suture on the first side of the surgical buttress. While only one loop is shown for the attachments to the distal ends of the elongate members, in some embodiments multiple loops are used. In this example elongate member 509 is the anvil but either the anvil or the staple cartridge can be stationary. Surgical buttress 530 has a length such that when it is folded (on the fold line), it is slightly less than the distance between the distal end of elongate members 507 and 509 and opening 552 and is also shorter than the distance between the distal end of the elongate members and the pivot point. Suture 554 is advanced though one opening 552, through the inside of the fold of folded surgical buttress 530, and out the opening 552 on the other side of the stationary elongate member (not shown). As this length of suture is tightened, the suture will pull on the fold line of surgical buttress 530 causing it to be stretched (as the distal ends are held in place by suture loops 550). A knot or other enlargement is provided to keep suture 554 from pulling through openings 552.

Figure 6:
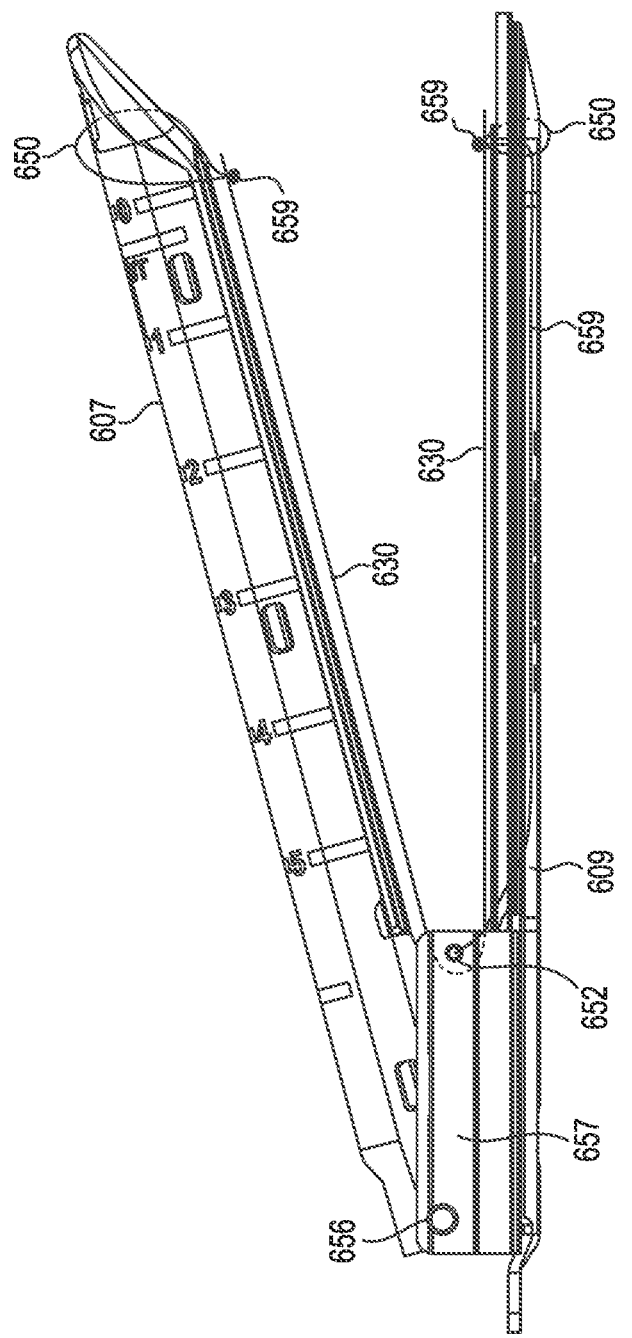
FIG. 6 is a schematic diagram of a surgical buttress releasably attached to the elongate members accordance with a number of embodiments of the present disclosure.

FIG. 6 is a schematic diagram showing an embodiment of surgical buttress 630 mounted on elongate members 607 and 609. Elongate members are connected to each other at pivot point 656. In some embodiments the pivotably connected elongate members are referred to as the jaw assembly. The proximal end of one of the elongate members has side extensions 657 that extend above the surface of the elongate member with openings 652 positioned in the side extensions that is distal to pivot point 656. A length of suture 659 is used to attach surgical buttress 630 to the elongate members. At the distal end of one of first of elongate members, a loop of suture 659 is formed and positioned through the anchor points (not shown) and around the distal end of the first elongate member. The suture 659 is then fed through openings 652 in the assembly and then to the distal end of the second elongate member. In FIG. 6, the length of the suture that runs along the second elongate member is not shown as it would be on the back of the jaw assembly in the figure. At the distal end of the second elongate member, the suture 659 is tightened and a second loop is formed. Surgical buttress 630 has a length such that when it is folded, it is slightly less than the distance between the distal end of elongate members 607 and 609 and openings 652. As suture 659 is tightened, the suture will pull on the fold line of surgical buttress 630 causing it to be stretched (as the distal ends are held in place by the end sections of suture 659). While only one loop of suture material is shown at the distal end of each elongate member, in some embodiments multiple loops can be used.

Figure 7:
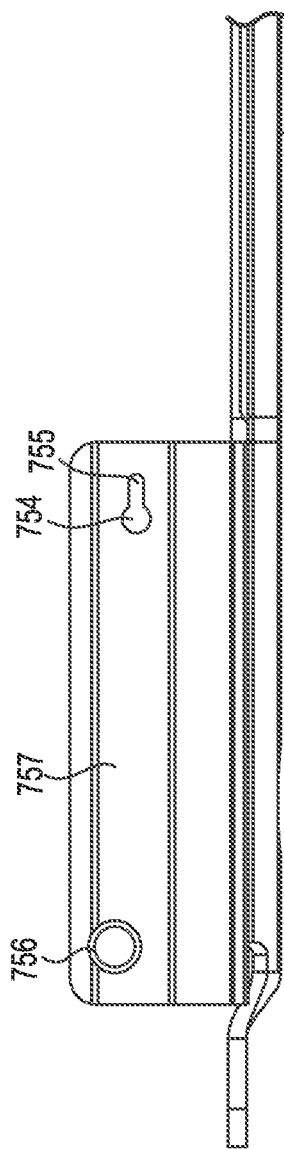
FIG. 7 is a schematic diagram the proximal end of an elongate member in accordance with a number of embodiments of the present disclosure.

FIG. 7 is a schematic diagram the proximal end of an elongate member in accordance with a number of embodiments of the present disclosure. Elongate member 709 includes side extension 757 having an opening, or keyhole, 755 is positioned distal to each opening 754. After the suture material has been used to attach the surgical buttress to the elongate members, the suture is moved from opening 754 to keyhole 755. Keyhole 755 is sized to be smaller than opening 755 and also sized such that, while the suture material can be pushed into the keyhole, it will stay there due to friction. As will be discussed later, when the suture material is cut, any suture material positioned in keyhole 755 will stay attached to the elongate member.

Figure 8:
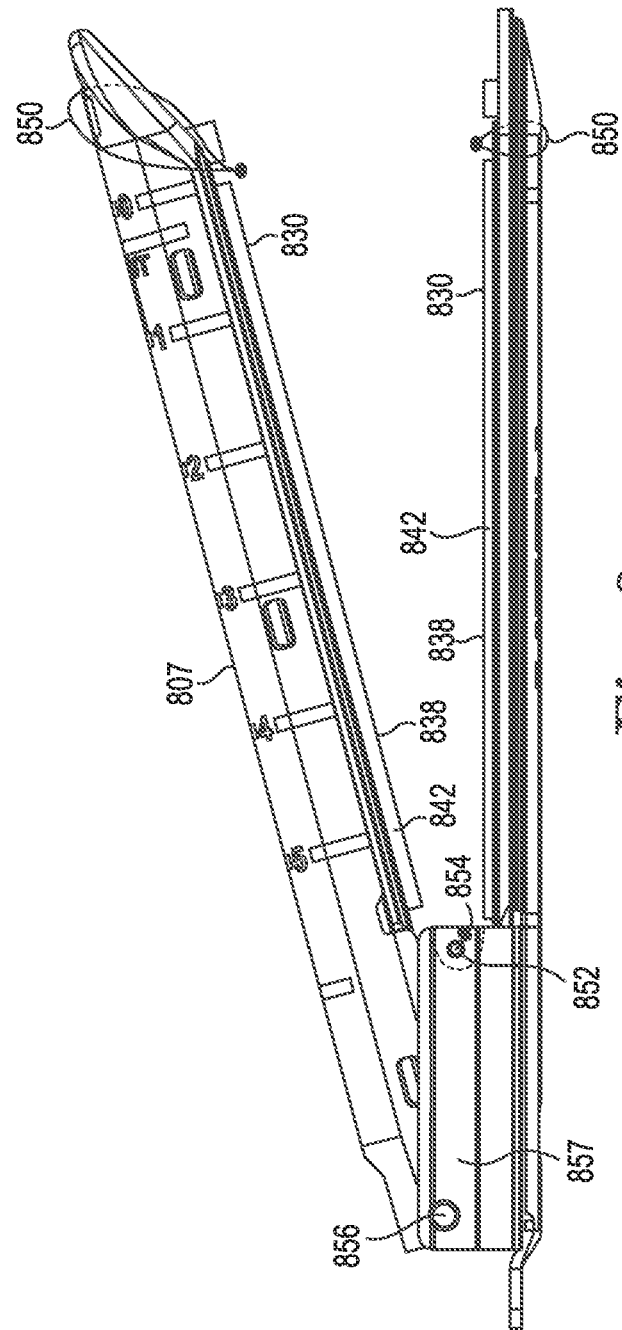
FIG. 8 is a schematic diagram of a surgical buttress releasably attached to the elongate members accordance with a number of embodiments of the present disclosure.

FIG. 8 is a schematic diagram showing an embodiment of surgical buttress 830 releasably mounted on elongate members 807 and 809. In this embodiment, surgical buttress has a width that allows it to be folded over and away from the surface of elongate member 807 and 809. After the surgical buttress 830 is positioned on elongate members 807 and 809, it is folded along axial fold line 838. Folded sections 842 extend at an approximate 90° angle away from the surface of the elongate members. Elongate members are connected to each other at pivot point 856. The proximal end of one of the elongate members has side extensions 857 that extend above the surface of the elongate member with openings 852 positioned in the side extensions that is distal to pivot point 856. A distal suture loop 850 is formed at the distal end of both elongate members. A length of suture material 859 is advanced through anchor points (not shown) and around one of the anvil or staple cartridge. The suture material is then tied or joined to make loop 850. This is done for both the anvil and staple cartridge. In some embodiments the suture material is not a complete loop but can be held in place by a knot positioned on the side of the surgical buttress that is opposite the surface of the anvil or staple cartridge. In this embodiment, loop 850 extends from a first side of the surgical buttress through an anchor point, around the anvil or staple cartridge, and back through the other anchor point, with a knot or other enlargement of suture material positioned at each end of the suture on the first side of the surgical buttress. While only one loop is shown for the attachments to the distal ends of the elongate members, in some embodiments multiple loops are used. In this example elongate member 809 is the anvil but either the anvil or the staple cartridge can be stationary. Surgical buttress 830 has a length such that when it is folded (on the fold line), it is slightly less than the distance between the distal end of elongate members 807 and 809 and opening 852 and is also shorter than the distance between the distal end of the elongate members and the pivot point. Suture 854 is advanced though one opening 852, through the inside of the fold of folded surgical buttress 830, and out the opening 852 on the other side of the stationary elongate member (not shown). As this length of suture is tightened, the suture will pull on the fold line of surgical buttress 830 causing it to be stretched (as the distal ends are held in place by suture loops 850). A knot or other enlargement is provided to keep suture 854 from pulling through openings 852.

Figure 9B:
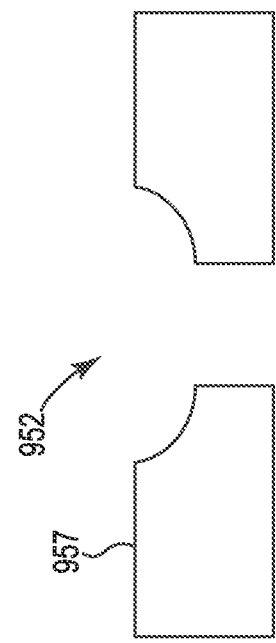
FIGS. 9A and 9B are schematic diagrams of examples of the cross section of an opening.
Figure 9A:
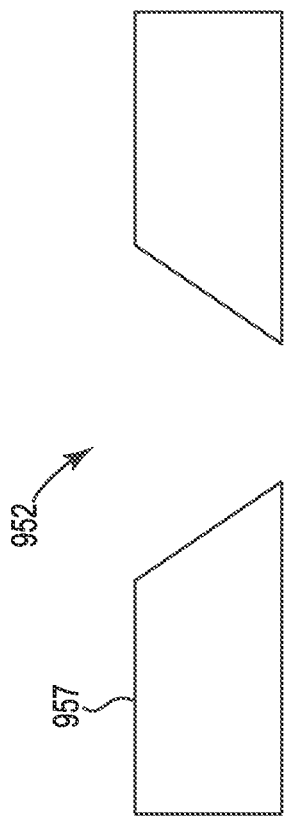

FIGS. 9A and 9B show example cross sections of opening 952 in side extension 957 in accordance with some embodiments. These figures show opening 952 with a chamfered (chamfered, beveled, or angled) cross section. In FIGS. 9A and 9B the side of the opening that faces away from the jaw assembly has a larger diameter than the side of the opening that faces the jaw assembly. While the opening shown here is circular, other shapes can be used.

In some embodiments described herein, the sutures or suture loops are attached to the stapler by melting the suture material. In these embodiments, the distal suture attachments around the distal end of the staple cartridge and anvil are formed by placing a length of suture around the cartridge and/or anvil with the ends placed on the surgical buttress. The suture material is then heated and pressed into the surgical buttress. For the proximal connection, the first end of the surgical material can either be melted to form an enlarged end on the suture material or a knot can be tied to form the enlarged end. As described above, the second end of the length of suture is fed through the first opening, placed distal of the fold line of the surgical buttress, and out the other opening. The second end is tensioned to pull the surgical buttress fold line toward the proximal end of the device (and to tension the surgical buttress) and a knot or other enlargement of the suture is formed. Using a heated device, the enlarged ends of the proximal attachment suture are scraped to form an enlarged end that is flush with the outer edge of the opening.

In some staplers, the distal end or tip of the anvil, distal of the anvil surface used to form the staples, has a pointed shape. In the tip region, the circumference (the length around the structure) of the anvil tip is less than a circumference of the anvil in the area of the anvil surface. In some staplers, the distal end or the tip of the staple cartridge has a surface that slopes away from the surface (the location of the staples) of the staple cartridge to form a flat point. In the tip region, the circumference of the tip is less that a circumference of the staple cartridge in the area of the surface. In some embodiments, when attaching the distal suture loops to the anvil and staple cartridge, the loops are formed in the area of reduced circumference. Then, when the proximal suture is tensioned resulting in a proximal facing tension on the surgical buttress, the distal suture loops will tighten allowing for any slack in the surgical buttress to be removed. In some embodiments, the length of the buttress is such that it extends to the smaller circumference section of the anvil and/or staple cartridge.

Figure 10A:
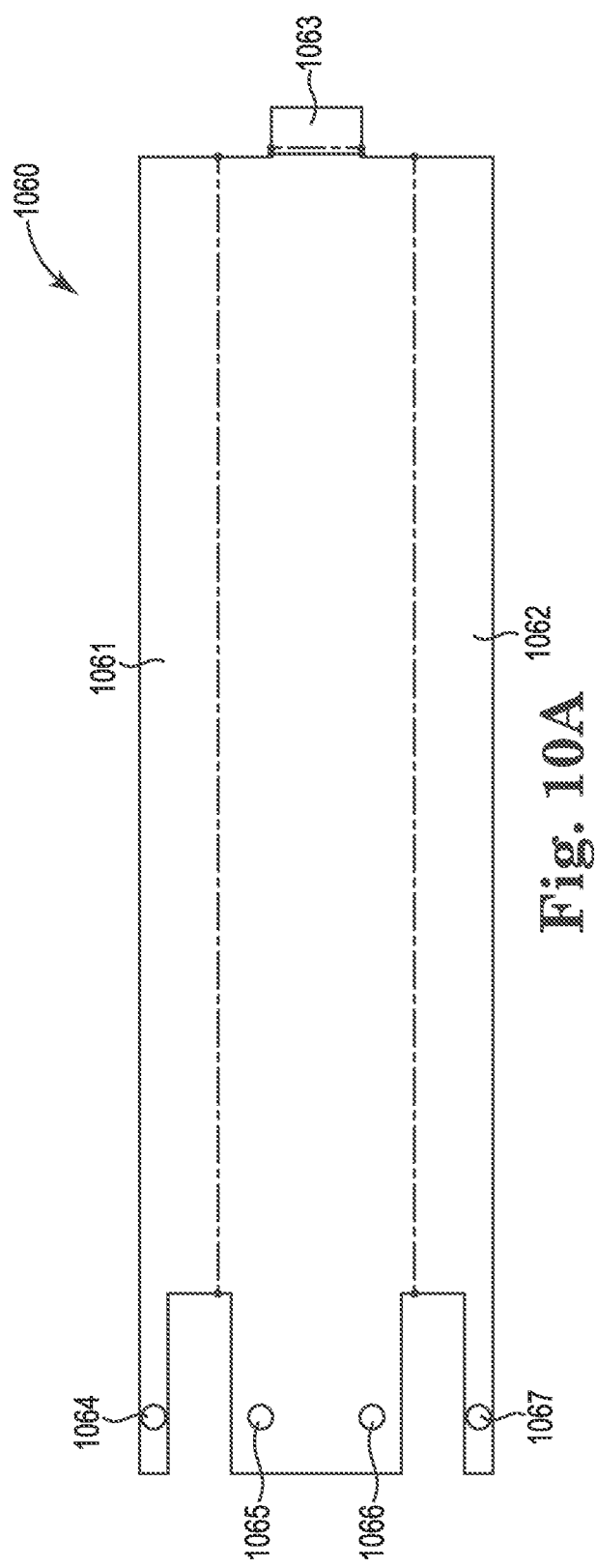
Figure 10B:
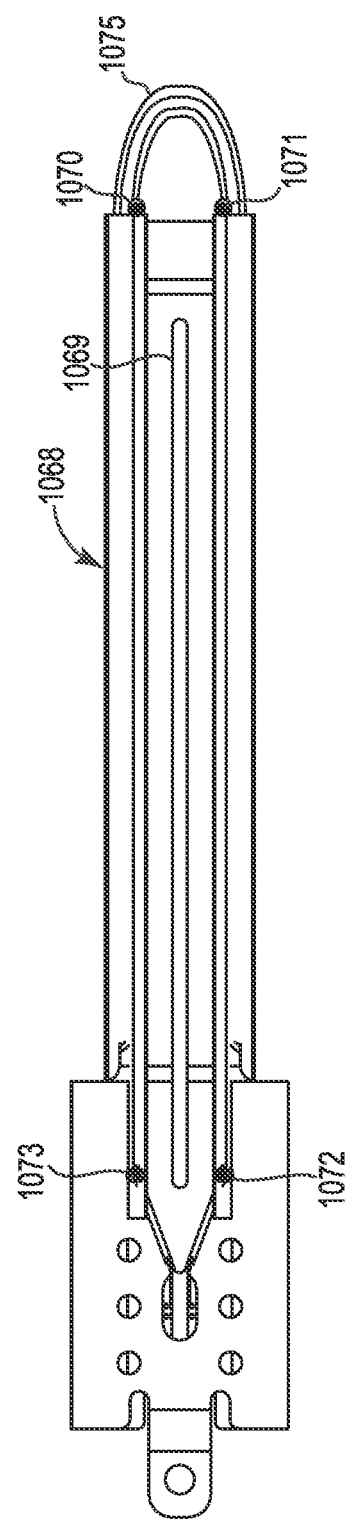

In some embodiments, the buttress will comprise two pieces—an anvil buttress and a cartridge buttress. FIGS. 10A, 10B, and 10C show one embodiment of an anvil buttress and the anvil. FIG. 10A shows a flat view of the buttress material 1060 which comprises a first bead section 1061, a second bead section 1062, and distal tab 1063. The proximal end of buttress material 1060 comprises holes or openings 1064, 1065, 1066, and 1067. In some embodiments, holes or openings 1065 and 1066 are referred to as surface openings or holes as they are positioned on the surface on anvil 1068 when assembled. In some embodiments, openings or holes 1064 and 1067 are referred to as lateral openings or holes and they are positioned on the side of anvil 1068 when assembled. FIG. 10B shows a top view (the face) of anvil body 1068, which can be either elongate member 107 or 109, shown in FIG. 1. Anvil body 1068 includes slot 1069 in which an I-Beam (not shown) will be positioned during use, distal holes 1070 and 1071, proximal holes 1072 and 1073, and distal tip 1075. FIG. 10C is a side view of anvil body 1068 with buttress material 1060 mounted thereon. Shown is first bead section 1062 positioned on the side of anvil body 1068, and cleat (e.g., cinch) 1074. Cleat may be stamped from the material of the anvil or may a separate piece of material that is welded, glued, or bonded to the anvil. Buttress material 1060 is secured to the anvil via suture 1073. In some embodiments, the top of tip 1075 will not extend as high as the face of anvil body 1068 so that a step is formed between the two surfaces. In some embodiments, suture 1073 is a length of biodegradable and/or biostable suture material with a loop formed at one end.

To mount buttress material 1060 onto anvil body 1068, the buttress material is positioned on the flat, top surface of the anvil (face) and first (e.g., left) bead section 1061 and a second (e.g., right) bead section 1062 are folded at an approximate 90° angle over the sides of the anvil. The free (non-looped) end of suture 1073 is threaded up through hole 1070, positioned on top of distal tab 1063, and down through hole 1071. In embodiments where there is a step down from the face of anvil body 1068 to the anvil tip 1075, the suture is positioned on the anvil tip. In this embodiment, the step prevents the suture from being moved proximally along the face of the anvil. Suture 1073 is then positioned along the side or underside of anvil 1060 such that right bead material 1062 is positioned between the suture and the anvil (as shown by the dotted line portion of suture 1073). The free end of suture 1073 is then threaded through hole 1067 in the buttress material, through anvil hole 1072, and then through buttress hole 1066. Suture 1073 then crosses anvil slot 1069 and is threaded down through buttress hole 1065, anvil hole 1073, and then through buttress hole 1064. Next, the free end of suture 1073 is threaded through the looped end of the suture such that second bead material 1061 is positioned between the suture and anvil body 1068. The free end of suture 1073 is pulled to tighten the entire length of the suture and the free end in positioned in and/or around cinch 1074 to secure the suture. Any excess suture material may be trimmed off. In some embodiments, suture 1073 does not have a looped end. In this embodiment, the two end of the suture will be drawn to remove slack in the suture and then the two ends tied or connected together. In this embodiment, both or one end may be positioned in and/or around cinch 1074 to secure suture 1073.

At this stage, the anvil section of buttress 1060 is tight and flat across the anvil face and the suture is securing distal tab 1063 to the tip of the anvil. The left and right bead sections of the buttress are folded over the side and/or bottom of the anvil and positioned between the anvil and the suture. At the proximal end, the suture crosses over the anvil slot and pins the buttress to the anvil face. When a physician/user uses a surgical stapler 100 with the anvil buttress, the blade of the I-Beam will cut the proximal suture positioned over slot 1069 and between holes 1072 and 1073. At this point, the suture will become slack and the distal tab 1063 will not be held down. After the physician/user has completed the stapling process and removes the surgical stapler from the patient, the suture material will be removed from the body with the stapler and the buttress material 1060 will remain in the body as a result of being stapled to the body tissue by the staples of the surgical stapler.

Figure 11B:
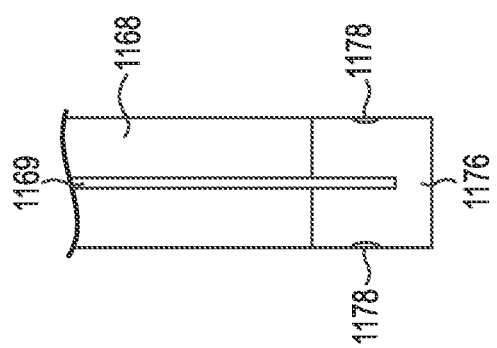
FIGS. 11A, 11B, 11C, and 11D are schematic diagrams of example aspects of the buttress material and an anvil.
Figure 11A:
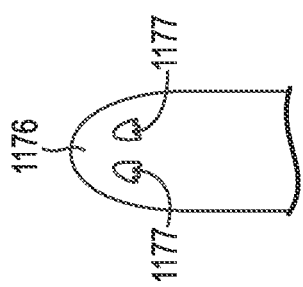

FIGS. 11A, 11B, 11C, and 11D show aspects of another embodiment of the anvil buttress. In this embodiment, the buttress material is the same as shown in FIG. 10A. Shown in FIG. 11A is the distal end of anvil cover 1176 which covers the bottom of anvil body 1168. Positioned near the distal end of anvil cover 1176 are two openings and cinch points 1177. FIG. 11B is a view of the proximal end of the top (face) of anvil body 1168, shown with slot 1169. Two proximal cinch points 1178 are formed on the interior of anvil cover 1176.

To mount the buttress material to anvil body 1168, a piece of suture is fed through one of hole 1070 or 1071, positioned across the top of distal tab 1063, and then through the other of hole 1070 and 1071 of the anvil. The suture is tightened, and the two ends are attached to the two cinch points 1177. To attach the proximal end, a length of suture is fed through hole 1067, through hole 1072, through hole 1066, across the top of suture 1060 (which is positioned above slot 1169), through hole 1065, then through hole 1073, and finally through hole 1064. The suture is then tightened, and the two ends are attached to the two cinch points 1178.

Figure 11D:
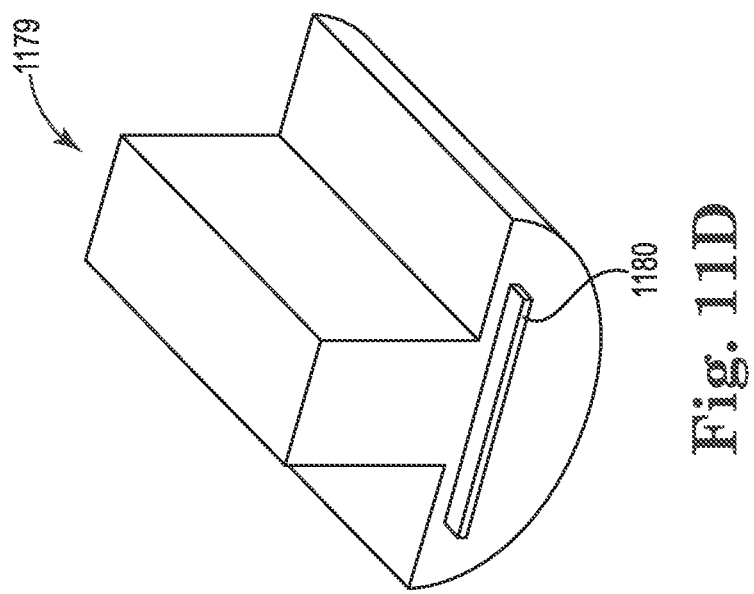
Figure 11C:
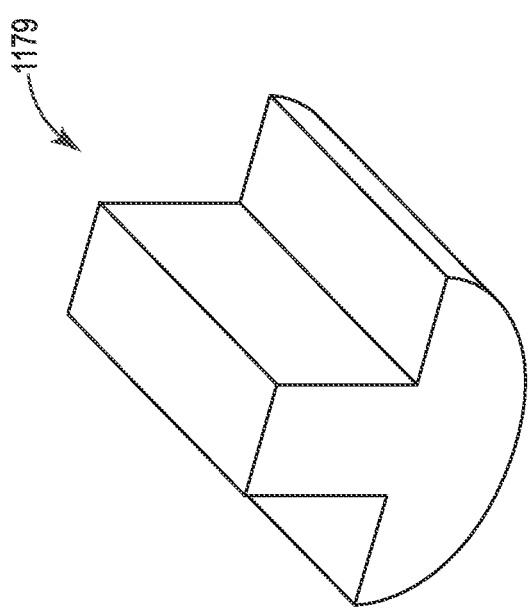

FIG. 11C shows an anvil insert 1179. Anvil insert 1179 is positioned between anvil body 1168 and anvil cover 1176 and is moveable within the anvil. Anvil insert 1179 is positioned distal to the I-beam (not shown) so that the anvil insert is moved distally as the user/physician delivers staples from the surgical stapler. As the user/physician begins to deliver staples (and move the I-beam distally), the cutting edge of the I-beam will cut the proximal suture. As the last staples are being delivered and the I-beam has moved to its distal most position, the distal end of anvil insert will enter distal tip 1075 of anvil body 1168 and push the suture that is positioned in cinches 1177 distally, releasing the suture. When the physician/user removes the surgical stapler from the body, the proximal and distal suture will also be removed.

FIG. 11D shows another embodiment of anvil insert 1179. In this embodiment, the distal end of anvil insert has knife edge 1180. In this embodiment, as the last staples are being delivered and the I-beam has moved to its distal most position, the distal end of anvil insert will enter distal tip 1075 of anvil body 1168 and knife edge 1180 will cut and release the distal suture.

Figure 12A:
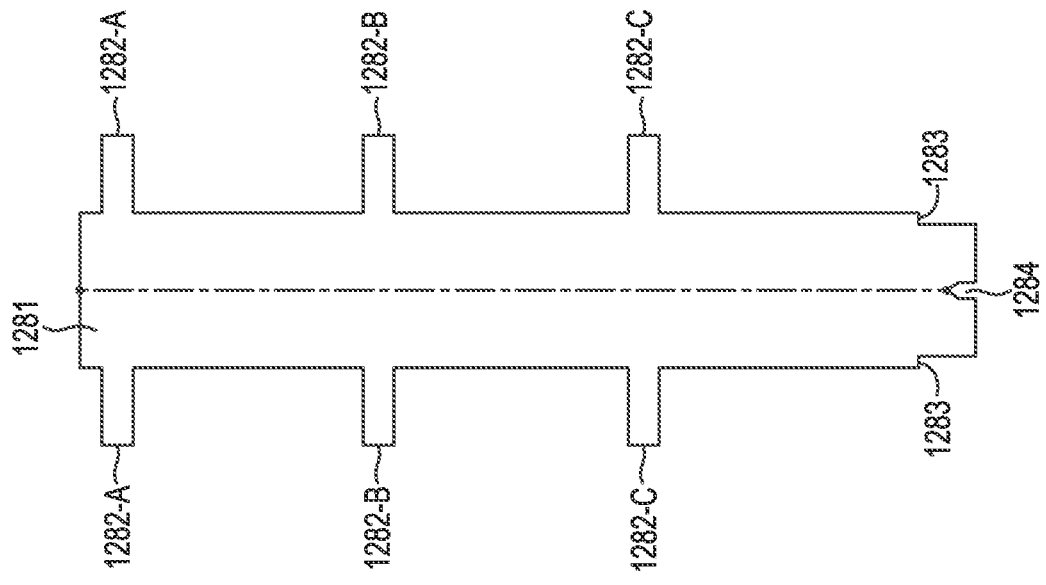
FIGS. 12A and 12B are examples of buttress material configured for placement on a staple cartridge.
Figure 12B:
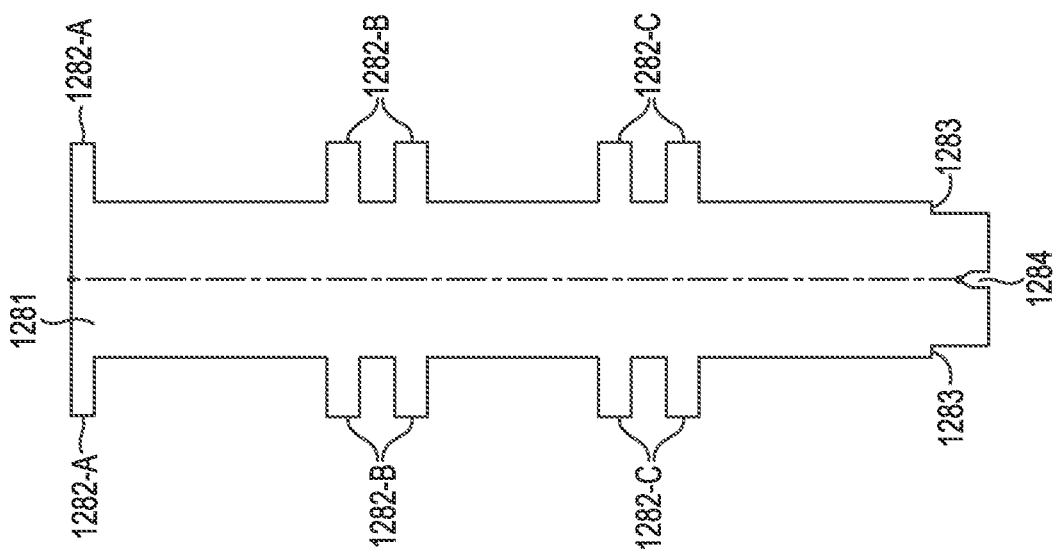
Figure 13A:
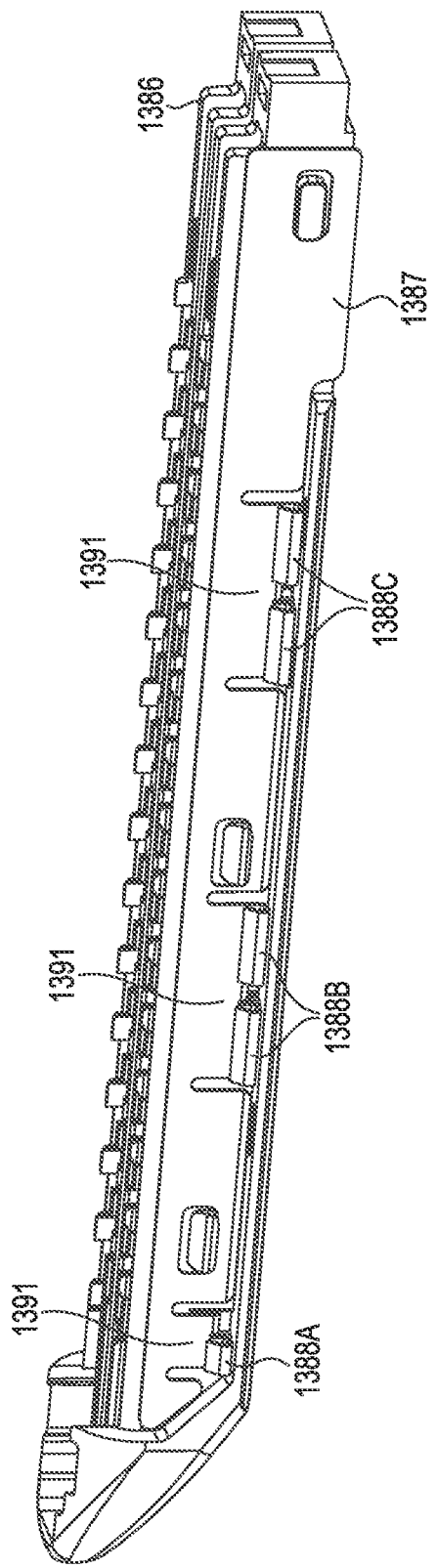
Figure 13B:
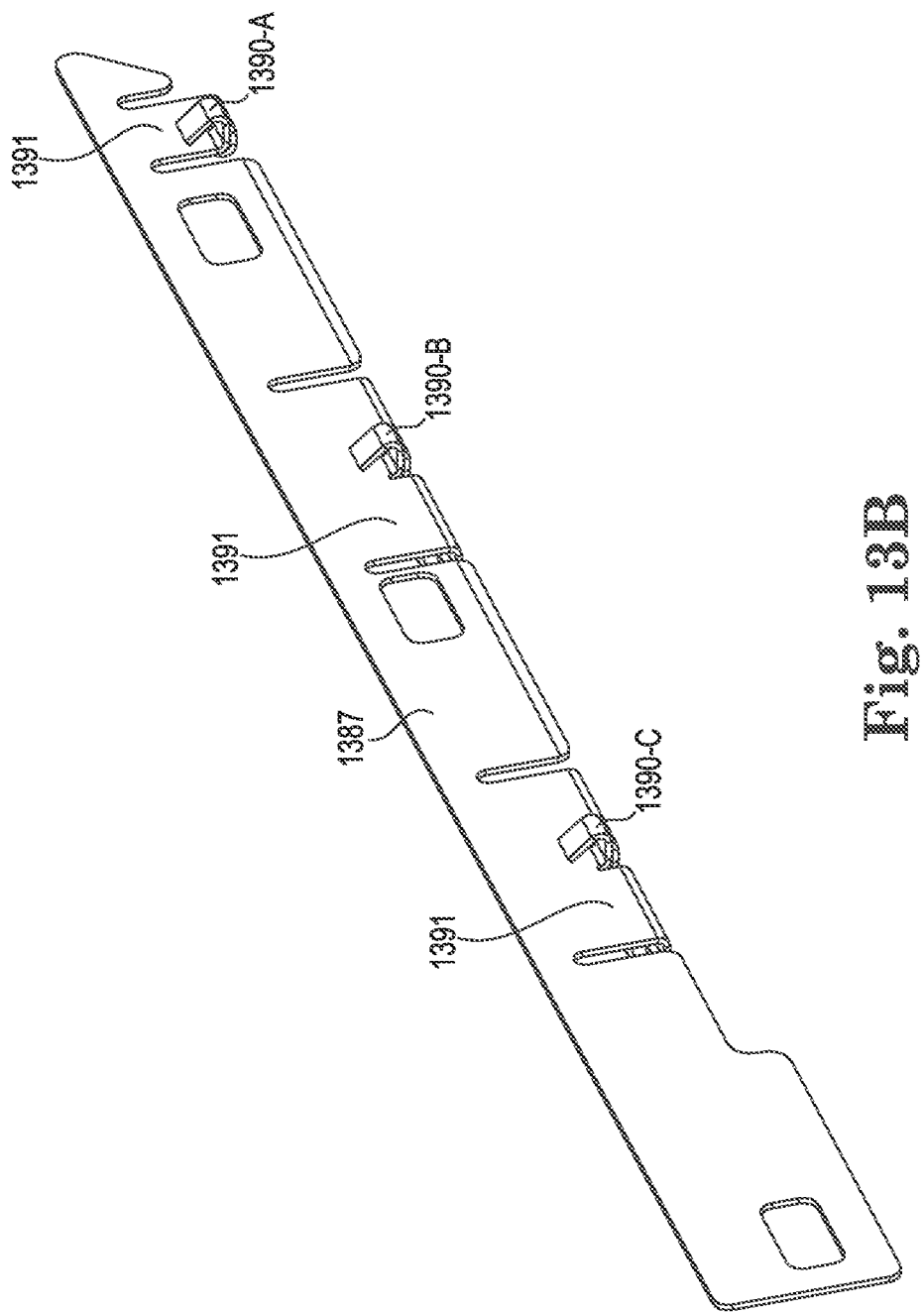

FIGS. 12A and 12B show examples of cartridge buttress material 1281, in accordance with a number of embodiments of the present disclosure. Buttress 1281 includes distal retention or buttress tab 1282A, middle retention or buttress tab 1282B, and proximal retention or buttress tab 1282C. In FIG. 12A there are two buttress tabs at each location and on each side of the buttress material whereas in FIG. 12B there is only one buttress tab at each position. While one or two tabs are shown at each point, more tabs at each position or tabs at additional positions could also be used. In some embodiments, buttress 1281 will include proximal cutouts 1283 so that the proximal section of the buttress will be positioned within the raised edges of the face or top of the staple cartridge. In this embodiment, all of the tabs 1282 are positioned distal of the distal end of the raised edge so that they tabs can be folded over the side of the staple cartridge. In some embodiments, buttress 1281 will include a perforation line where the cutter of the I-beam will travel during staple delivery. In some embodiments, buttress 1281 will also include a cut out 1284 corresponding to the shape of the cutting edge of the I-beam (not shown). While FIG. 12A shows two retention or buttress tabs at various locations along the length of buttress 1281, in some embodiments 1, 2, 3 or more tabs at each location can be used. While FIGS. 12A and 12B show tabs at three locations (proximal, middle, distal), in some embodiments only two locations are used and, in some embodiments, more than three locations can be used. In some embodiments, a minimum of two retention or buttress tabs on each side of buttress 1281 are used. 100471 FIGS. 13A and 13B show embodiments of the staple cartridge in accordance with a number of embodiments of the present disclosure. Shown in FIG. 13A is staple cartridge body 1386 and the exterior of plate 1387. Shown on this side of plate 1387 are external raised portions or projections 1388. In this embodiment, there are five raised exterior portions or projections 1388, 1388A at a distal position, 1388B at a middle position, and 1388C at a proximal position. In some embodiments, there can be 1, 2, 3, 4, 5, 6, or more raised portions. The raised portions 1388 are positioned on flap 1391, which is a portion of plate 1387 that is connected to plate 1387 on only one side (e.g., includes 3 unconnected edges). This allows the flap in in the area of the unconnected edges, to flex or bend away from the plane of the plate as will be discussed below. FIG. 13B shows the inside surface of plate 1387. When assembled, the inside surface of cover 1387 will be positioned adjacent to the exterior surface (shown in 13A) staple cartridge body 1386. Positioned on the inside surface of cover 1387 are interior raised portions or projections 1390. In some embodiments, these raised portions include a section that extends away from the surface of cover 1387 followed by a curve and a section that extends back toward the surface of the cover. Shown is distal interior raised portion 1390A, middle raised interior portion 1390B, and proximal interior raised portion 1390C. The raised portions 1390 are positioned on the inside of flap 1391. In the shown embodiment, distal interior raised portion 1390A is positioned adjacent distal exterior raised portion 1388A; middle raised interior portion 1390B is positioned between middle exterior raised portions 1388B, and proximal interior raised portions 1390C is positioned between proximal exterior raised portion 1388C.

In some embodiments, the number of exterior raised portions 1388 will correspond to the number of tabs 1282 on buttress 1281 of FIGS. 12A and 12B. In some embodiments, buttress tabs 1282 of FIGS. 12A and 12B are aligned with and positioned under raised portions 1388 and between flap 1391 and the body of staple cartridge 1386 when buttress 1281 is mounted on staple cartridge 1386. In some embodiments, raised exterior portions 1388 are positioned adjacent to interior raised portions 1390 and they do not overlap in a longitudinal direction. In some embodiments, the number of interior raised portions 1390 will correspond to the number of tabs 1282 on buttress 1281 of FIGS. 12A and 12B. In some embodiments, at least two left and at least two right buttress tabs are provided and at least two right side flaps and at least two left side flaps, each with at least one interior raised portion or projection, are provided.

Figure 13C:
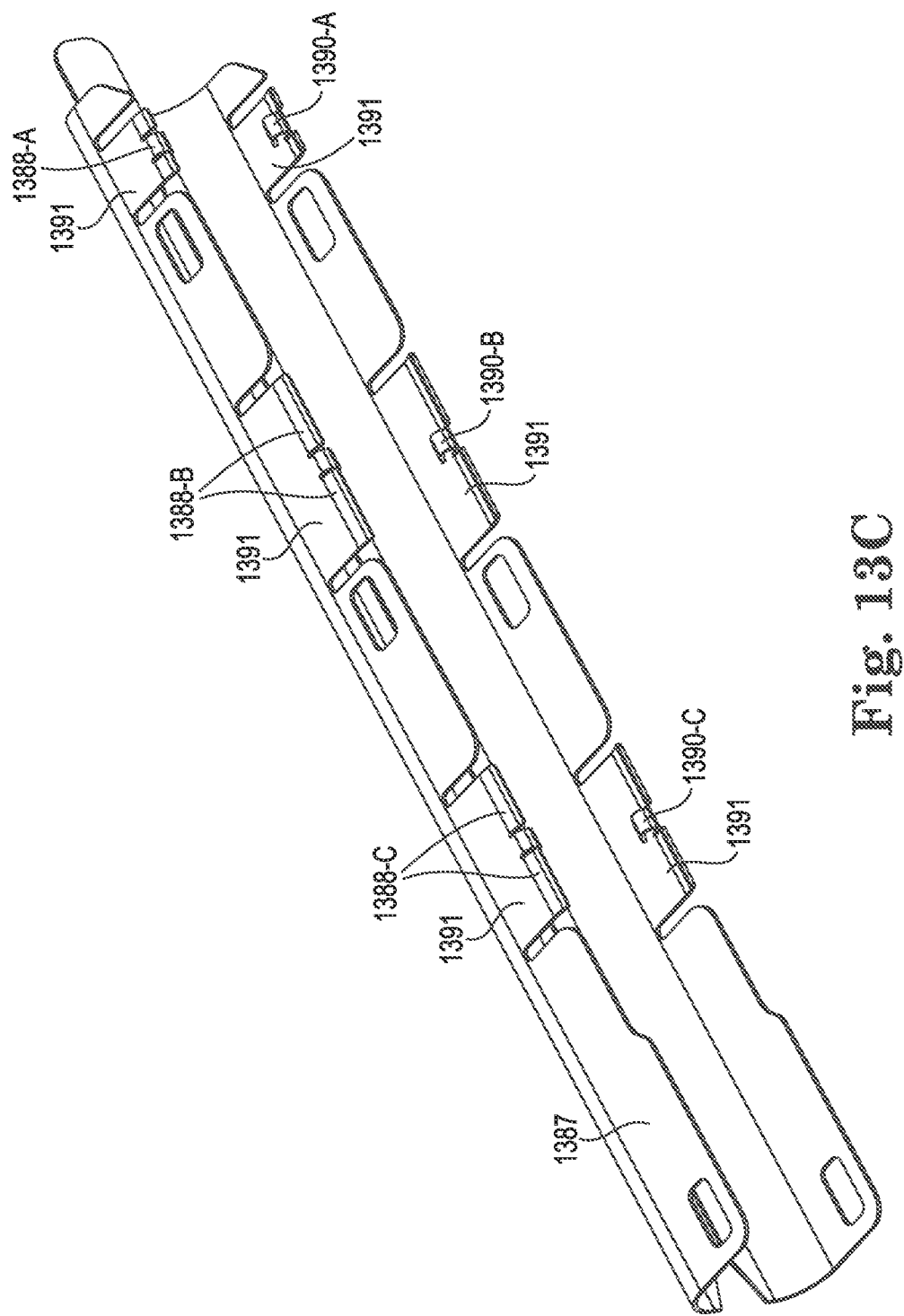

An embodiment of a plate of the disclosure of the present invention is shown in FIG. 13C. Shown in FIG. 13C is plate 1387. Shown are interior raised projections 1390, exterior raised projections 1388, and flaps 1391. This embodiment differs from the embodiment of FIGS. 13A and 13B in that instead of having a left plate and a right plate, the embodiment of FIG. 13C comprises a single plate, with left and right sections.

During the manufacturing/assembly of a staple cartridge assembly 103, a piece of buttress material 1281 will be positioned on the top or the face of staple cartridge body 1386 with portions of the material, including tabs 1282, being positioned on the sides of the body. A plate 1387 will be positioned on either side of cartridge body 1386 with each buttress tab 1282 positioned between the cartridge body and a flap 1391. Retention or buttress tabs 1282 are positioned between raised projections 1388 and cartridge body 1386 and held in place by the friction of flaps 1391 and the surface of cartridge body 1386. Preferably, raised projections in the area of where the tab is being held are rounded so that upon release tabs 1282 will not catch on the raised projections. After the plates or plate are positioned, a cover or bed (not shown) is placed over the plate or plates and the bottom (side opposite the face) of the cartridge body 1386. External raised projections 1388 extend through openings in the cover or bed. In some embodiments, exterior raised projections 1388 have curved surfaces in order to not catch the buttress 1281 as the tabs are released.

FIG. 13D is an example showing delivery of staples and the release of a buttress. During delivery of the staples, as an I-beam (not shown) and staple driver 1393 are moved distally, the staple driver will apply outward pressure on interior raised portions 1390 which in turn will apply outward pressure on flaps 1391. Outward movement of flaps 1391 will result in the release of retention or buttress tabs 1382 and the release of buttress 1381. Also shown are staples 1392 and cover or bed 1389.

In some embodiments, buttress tabs 1282 in FIGS. 12A and 12B may comprise left and right buttress tabs 1282, corresponding to the orientation of the buttress when positioned on the staple cartridge. In some embodiments, plate 1387, shown in FIGS. 13A and 13B, may comprise left and right plates 1387, with left and right flaps 1391, left and right interior raised portions or projections 1390, and left and right exterior raised portions or projections 1388. In some embodiments, plate 1387 shown in FIG. 13C will comprise a left and right side.

Figure 14A:
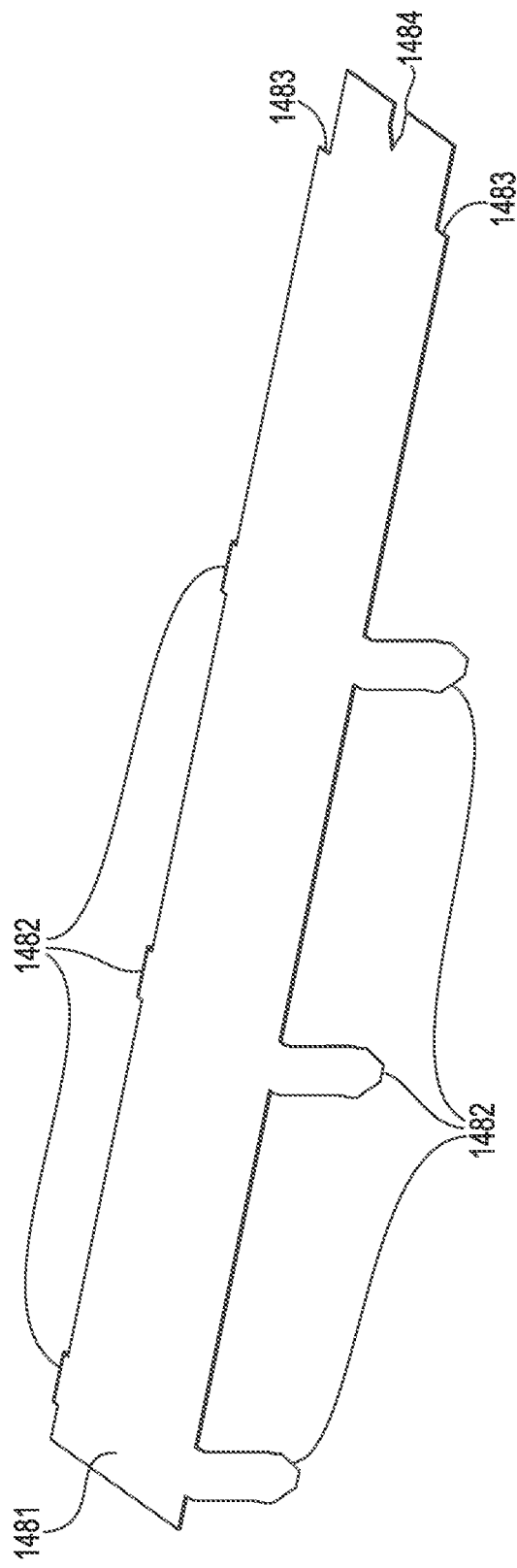
Figure 14B:
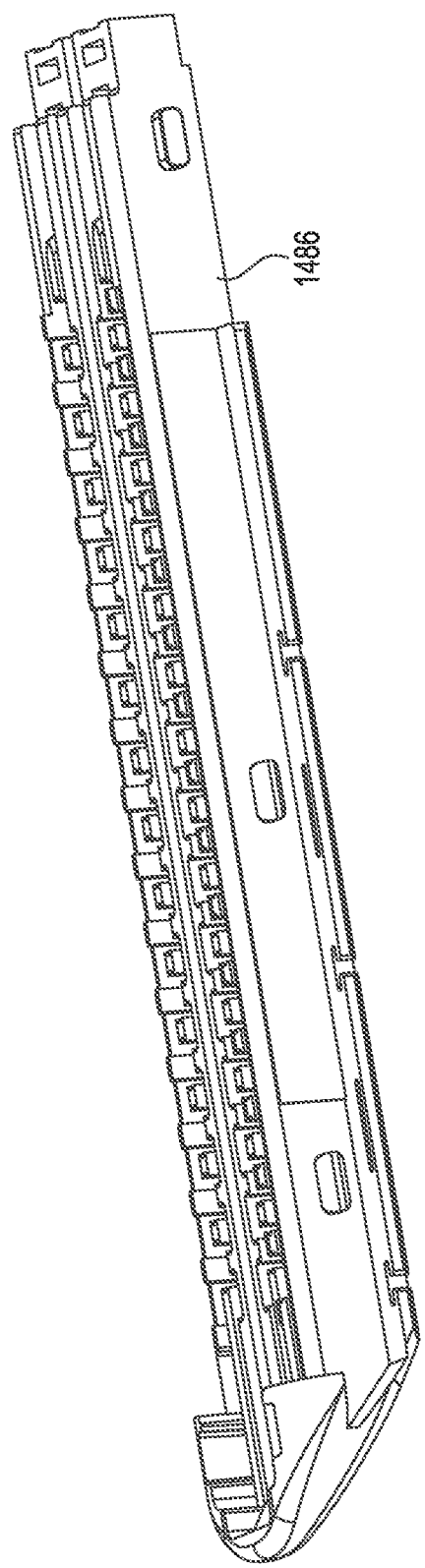
Figure 14C:
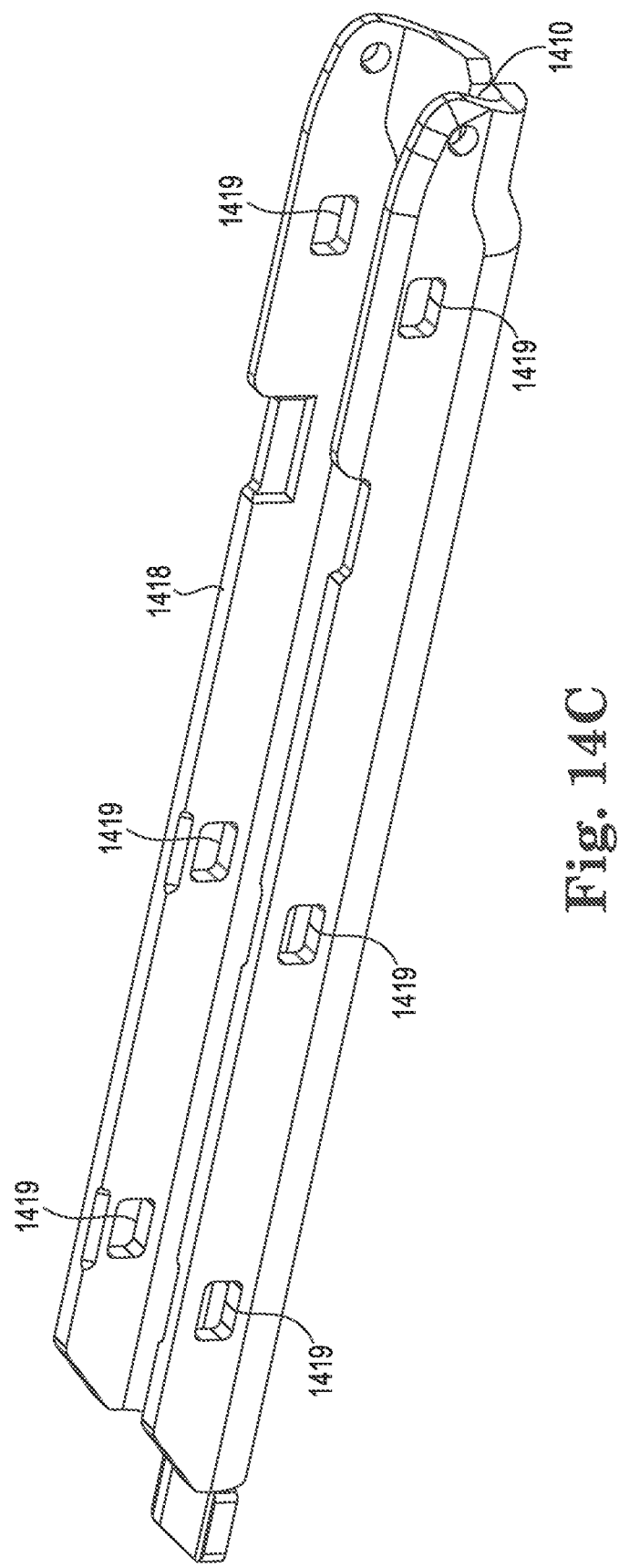
Figure 14D:
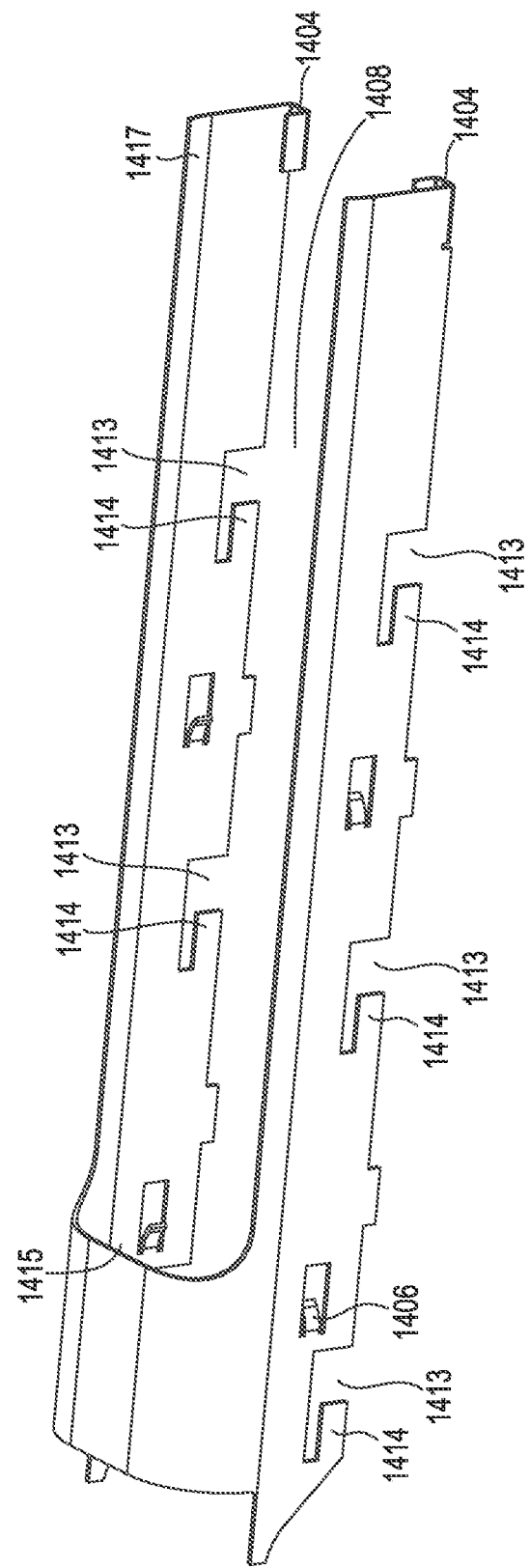

FIGS. 14A, 14B, 14C, 14D, 14E, 14F, 14G, 14H, and 14I show an example of a buttress and a staple cartridge in accordance with a number of embodiments of the present disclosure. Buttress 1481 is shown in FIG. 14A. Buttress 1481 includes buttress or retention tabs 1482. In some embodiments, cut outs 1483 and/or 1484 are present. Shown in FIG. 14B is the staple cartridge body 1486. Shown in FIG. 14C is staple cartridge bed 1418 and one or more openings 1419. I-beam slot 1410 extends almost the entire length in bed 1418. Shown in figure F4D is moveable cover 1417. Cover 1417, which can generally be described as a three-sided object, includes longitudinal opening 1408 that terminates at edge 1415. Positioned on the edges of cover 1417 are tabs 1414 and adjacent openings 1413. As shown, in some embodiments, openings could be described as a connected small and a large rectangle, or as an opening with a large and a small part or section. In some embodiments, openings 1413 can be described as a left-side opening and a right-side opening (one opening positioned on either side of cover 1417) wherein each opening comprises a first portion and a second portion. While three tabs 1414 and openings 1413 are shown on each side of cover 1417, 2, 3, 4, 5, or more tabs and openings can be used. In some embodiments, the number of tabs 1414 and openings 1413 will equal the number of tabs 1482 on buttress 1481. In some embodiments, tabs 1414 are positioned on both the right- and left-hand sides of cover 1417. In some embodiments, there are at least two tabs positioned on both the right and left sides of cover 1417 and at least two retention or buttress tabs 1482.

Figure 14E:
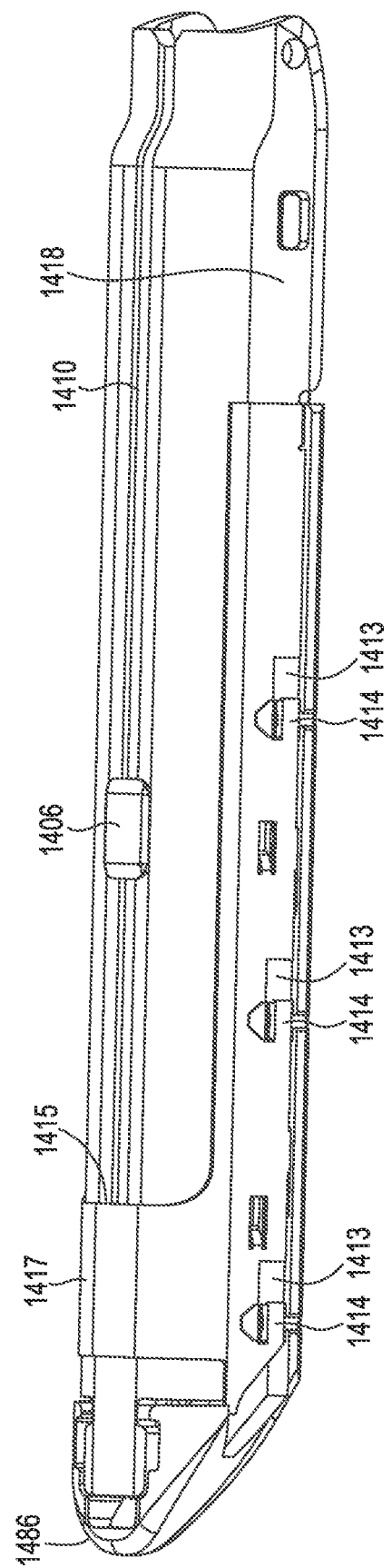
Figure 14F:
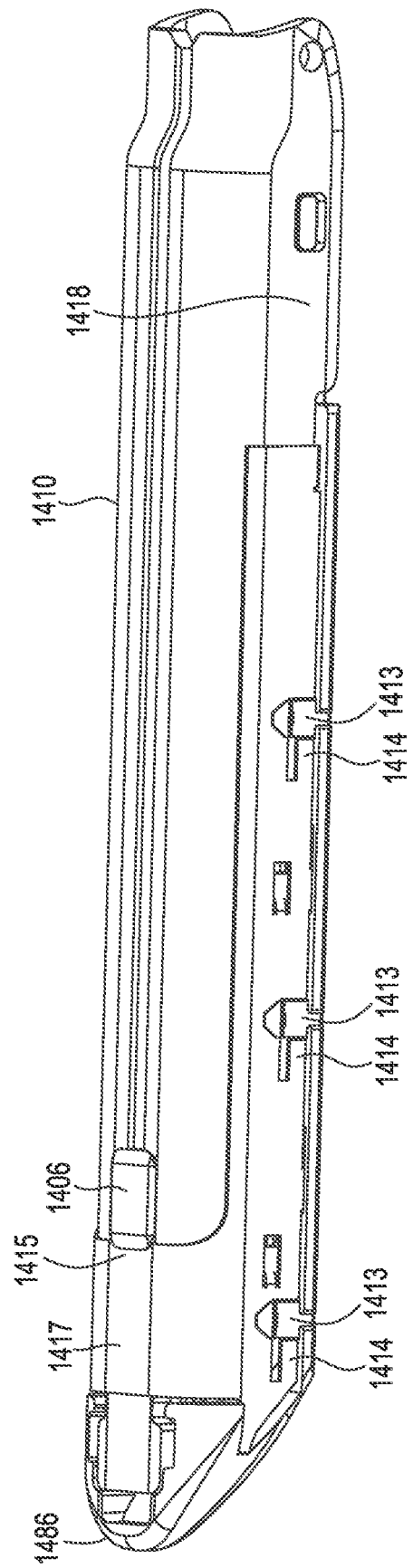

FIG. 14E shows a part of constructed staple cartridge assembly 103. Shown here is cover 1417 positioned over bed 1418 which is positioned over staple cartridge body 1486. As evidenced by I-beam 1406 positioned near the middle of the length of slot 1410, this view shows that about half of the staples have been delivered. Slot 1410 extends past and under edge 1415, as will be described later. Also shown are tabs 1414 and openings 1413. FIG. 14F is a view similar to 14E with the exception that I-beam 1406 is positioned at the distal end of slot 1410 indicating that all staples have been delivered. In this position, I-beam 1410 has pressed against edge 1415 of cover 1417 and moved it to a position distal to the position of the cover in FIG. 14E.

In some embodiments, as shown in FIG. 14G, retention feature 1406 of cover 1417 interacts with openings 1419 in bed 1418 to prevent inadvertent distal movement of cover 1417. As shown here, retention feature 1406 is positioned at the distal end of bed opening 1419. Inadvertent distal movement of cover 1417 relative to bed 1418 (and inadvertent release of buttress 1481) is prevented by the friction between retention feature 1406 and the distal end of bed opening 1419 and/or the interference between retention feature 1406 and the edge of bed opening 1419. When I-beam 1406 hits edge 1415, I-beam 1406 has sufficient force to overcome the friction between retention feature 1406 and the distal end of bed opening 1419 and cover 1417 is moved distally. Cover 1417 can be attached to the staple cartridge assembly is numerous ways, as is known in the art. One embodiment is shown in FIGS. 14H and 14I. FIG. 14H shows distal nose 1406 being positioned under a ledge of bed 1418. As will be explained later, when cover 1417 is attached to bed 1418, it is placed from the top in the orientation shown in FIG. 14H. FIG. 14I shows cover loops 1404 being positioned over a section of bed 1418. In some embodiments, loops 1404 are positioned in recesses 1404 in bed 1418. Like FIG. 14H, the orientation of FIG. 14I is that the cover is positioned on top of the cartridge body 1486 (with the cartridge face being at the bottom of the figure).

In the manufacture/assembly of the embodiment of FIGS. 14A to 14I, bed 1418 is attached to the non-face side of staple cartridge body 1486. Buttress 1481 is positioned on the face of staple cartridge body 1486 with buttress or retention tabs 1482 positioned on the sides of the bed/cartridge body assembly. Cover 1417 is placed on the top of bed 1418 and buttress or retention tabs 1482 are positioned through the small part of opening 1413 and behind tab 1414. At this point, buttress 1481 is held to the assembly by the friction of tab 1414 on buttress tab 1482 against bed 1418. In some embodiments, during the process of mounting cover 1417 to bed 1416, cover nose 1406 is positioned under a ledge of bed 1418, cover loops 1404 are looped over bed 1418, and retention feature 1406 is positioned within opening 1419 of bed 1418 (if any/all are used in the particular embodiment).

During use of the embodiment of FIGS. 14A to 14I, the user physician will advance the distal end of surgical stapler 100 to the proper location in a patient's body and clamp elongate members 107 and 109. Using either moveable handle 112 or an electric motor, I-beam 1406 will move distally, causing staple wedge or driver 1393 to move distally and deliver staples. When almost all of the staples have been delivered, I-beam 1406 will hit edge 1415. Delivering further staples by moving I-beam 1406 further distal will cause body 1417 to move distal. This will cause buttress tabs 1482, which had been positioned in the small part of opening 1413 and behind tab 1414 to be positioned in the large part of opening 1413 and out from behind tab 1414. At this point, buttress 1481 is no longer attached to the surgical stapler assembly.

In some clinical situations, the physician/user may decide, after they have delivered some staples, that they do not want to deliver all of the staples. An example of the stapler in this situation is the view of FIG. 14E. At this point, since body 1417 is still in the proximal position, buttress 1481 is still attached to the surgical stapler assembly and the user/physician cannot remove the assembly from the body (as the proximal end of buttress 1481 is stapled to body tissue and buttress 1481 is still attached to the surgical stapler assembly). In this instance, the physician user can position an elongate instrument such as a forceps or other tool against edge 1415 and/or in slot 1410, distal of 1406. By advancing the elongate instrument, the physician/user can apply distal pressure to edge 1415 to move cover 1417 distally. This distal movement will disconnect buttress from the surgical stapler assembly and the user/physician will be able to remove the assembly from the patient's body.

In the embodiments shown in FIGS. 14A to 14I, cover 1417 is shown being positioned on top (or bottom) or on the outside of bed 1418. The inventions of these figures are equally applicable to a construction where cover 1417 is positioned inside of bed 1418. In this embodiment, buttress tabs 1282 can be positioned between cover 1417 and tabs 1414 to releasable secure the cartridge buttress to the cartridge or between cartridge body 1486 and tabs 1414 to releasable secure the cartridge buttress to the cartridge. Cover 1417 and edge 1415 will be moved distally by a section of the I-beam that is within the staple cartridge.

In some embodiment described herein, a surgical buttress for a surgical stapler having a staple cartridge and an anvil is disclosed. The surgical buttress is configured to substantially overlie both the staple cartridge and the anvil. The surgical buttress has a first end, a middle section, and a second end with a distal staple cartridge attachment location at the first end, a distal anvil attachment location at the second end, and a proximal attachment location in the middle section. The distal staple cartridge attachment location is positioned for registering with a distal end of the staple cartridge, the distal anvil attachment location is positioned for registering with a distal end of the anvil, and the proximal attachment location is positioned for registering with a proximal end of the staple cartridge and the anvil.

In some embodiment described herein, a surgical buttress for a surgical stapler having a staple cartridge and an anvil is disclosed wherein the surgical buttress includes separate anvil and cartridge buttresses. The cartridge buttress is configured to substantially overlie the staple cartridge and the anvil buttress is configured to substantially overlie the anvil. Both pieces of surgical buttress have a first end, a middle section, and a second end. The distal anvil attachment location being positioned at the first end of the anvil buttress, and an optional middle attachment location in the middle section of the anvil buttress, and a proximal attachment location being position at the second end of the anvil buttress. The distal cartridge attachment location being positioned at the first end of the cartridge buttress, and an optional middle attachment location in the middle section of the cartridge buttress, and a proximal attachment location being position at the second end of the cartridge buttress. The distal staple cartridge attachment location is positioned for registering with a distal end of the staple cartridge, the distal anvil attachment location is positioned for registering with a distal end of the anvil, the proximal staple cartridge attachment location is positioned for registering with a proximal end of the staple cartridge, and the proximal anvil attachment location is positioned for registering with a proximal end of the anvil.

As disclosed herein, in some embodiments the surgical buttress may be disposed on the face or tissue contacting surface of the elongate members (the staple cartridge and the anvil).

In one embodiment, a method of using the disclosed stapler is provided. When positioning the stapler for use, either in open surgery or through an instrument such as a trocar, the clinician may need to rotate and/or articulate the elongated members to position them properly. As the stapler is used to clamp, staple, and cut tissue, in some instances the clinician needs to clamp and unclamp the elongated members to ensure that they are properly positioned. Once the elongated members are in position, the clinician will clamp the elongated members and deliver the staples. The cutter on the I-beam will cut the tissue, the suture material that extends along the fold line, and the surgical buttress as the staples are being delivered. After the staples are delivered, the clinician will remove the stapler from the body. This proximal movement of the stapler will cause the distal ends of the elongate members to be 'pulled out' of the suture loops that had attached the distal ends of the surgical buttress to the elongate members.

In one embodiment, after the stapler is properly positioned, the clinician will clamp the elongated members and deliver the staples. The cutter on the I-beam will cut the tissue, the suture material that extends across the path of the I-beam, and the surgical buttress as the staples are being delivered. In some embodiments, the I-Beam will move a cartridge cover distally to release the cartridge buttress. After the staples are delivered, the clinician will remove the stapler from the body.

In one embodiment, a method of attaching a surgical buttress to a surgical stapler is provided. A length of surgical buttress is positioned on the surfaces of both elongate members (the anvil and the staple cartridge). In this position, the surgical buttress extends from the distal end of one elongate member to the proximal end of both elongate members and then to the distal end of the other elongate member. The buttress is then removably attached to the elongate members. It is required that the buttress will stay with the staples after the staples have been deployed. As discussed herein, the buttress can be releasably attached to the elongate members by either one or multiple lengths of suture. In one embodiment, three lengths of suture are used. In some embodiments, there is a distal suture loop at the distal end of one elongate member and a distal loop at the distal end of the other elongate member with a length of suture places through openings at the proximal end of the jaw assembly and positioned distal of the fold line of the buttress material. In some embodiments, the two distal loops are positioned around the tips of the elongate members. In some embodiments, the proximal length of suture, when positioned and attached, provides a proximal tension on the surgical buttress. This tension may take any slack out of the surgical buttress so that is lays adjacent to the surface of the elongate members. This tension may aid in retaining the surgical buttress on the surface of the elongate members during use. In some embodiments, surgical buttress material that is wider than the surface of the surface of the elongate members may be used. This surgical buttress material may be heat set or pressed in a direction away from the surface of the elongate member. This too may assist in keeping the buttress material properly positioned during use.

In some embodiments, the fold line of the surgical buttress, the most proximal end of the folded buttress material, is positioned distal to the most proximal staples so that at least one staple is delivered prior to the surgical buttress being stapled. In other embodiments, the fold line of the surgical buttress is positioned so that at least the proximal leg of the first staple is positioned proximal to the fold line. In some applications it is important for the buttress material to be stapled down prior to being cut by the cutting edge of the I-beam.

The surgical buttress can be biocompatible and/or bioabsorbable. The surgical buttress can be made from polyesters, polytetrafluoroethylene, polyglycolic acid, polylactic acid, copolymers of glycolic and lactic acid, or the like. The surgical buttress can be pre-loaded (from the manufacturer)

or can be sold separately and applied by the user. The suture material can be biocompatible or biocompatible and bioabsorbable. The surgical buttress can be made from polyesters, polytetrafluoroethylene, polyglycolic acid, polylactic acid, copolymers of glycolic and lactic acid, or the like. In some embodiments, the anchor points are shown as holes in the surgical buttress. These points may be pre-formed holes or can be locations where a sharp object (a needle) is used to place the suture material through the surgical buttress or simply where the suture material is attached to the surgical buttress. In the embodiment described above that uses three separate pieces of suture to attach the surgical buttress to the elongate members, all three pieces can be of the same diameter, of different diameters, or the proximal piece can be of a larger diameter.

Some of the embodiments described herein have a handle assembly with a reloadable staple or cartridge assembly. The embodiments herein are equally applicable to a staple system where the reloadable cartridge is just a staple cartridge that is loaded into one of the elongated members.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled. The terms proximal and distal, as used herein, are from the perspective of the clinician or other user of the device. The terms left and right, as used herein, are from the perspective of a clinician or other user holding unit 100 in an upright position (with handle 116 on the bottom).

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A reloadable cartridge assembly, comprising:
a staple cartridge comprising a proximal and distal end, a surface, a plurality of staples, and a moveable cover;
an anvil comprising a proximal and distal end, a surface and two sides;
an I-beam configured to move through the staple cartridge and anvil;
an anvil buttress, positioned on the surface and sides of the anvil, with a top surface facing away from the surface of the anvil and releasably secured to the anvil with at least one suture; and
a cartridge buttress positioned on the surface and sides of the cartridge and releasably secured to the cartridge by positioning the cover in a proximal position;
wherein the I-beam is configured to move the cover of the staple cartridge distally to release the cartridge buttress from the staple cartridge.

2. The reloadable cartridge assembly of claim 1 wherein the anvil further comprises two proximal openings and two tip openings; wherein the anvil buttress comprises two surface openings, two lateral openings, and a distal tab; and wherein, when assembled, the two surface openings of the anvil buttress are aligned with the two anvil proximal openings.

3. The reloadable cartridge assembly of claim 2 wherein the at least one suture is positioned, sequentially, through a first tip opening, over the top of the distal tab, through the other tip opening, through a lateral opening, through a first anvil surface opening, through the anvil buttress, back through the anvil buttress, through the second anvil surface opening, and through the second lateral opening and, wherein, the suture is secured to the anvil.

4. The reloadable cartridge assembly of claim 1 wherein the staple cartridge further comprises a slot wherein a section of the I-beam is positioned within the slot and a portion of the I-beam is positioned on an exterior of the staple cartridge.

5. The reloadable cartridge assembly of claim 4 wherein the portion of the I-beam that is exterior to the cartridge interfaces with the edge to move the cover distally.

6. The reloadable cartridge assembly of claim 5 wherein the cover further comprises an edge, wherein the buttress comprises at least two right buttress tabs and at least two left buttress tabs, wherein the cover further comprises at least two left openings and at least two right openings, where each opening comprises a first portion and a second portion, and at least two left tabs and at least two right tabs, and wherein when the cover is in a proximal position, the cartridge buttress is releasably secured to the buttress due to the at least two left buttress tabs and at least two right buttress tabs being positioned between the at least two left tabs and at least two right tabs and a body of the staple cartridge.

7. The reloadable cartridge assembly of claim 6 wherein when the cover is in the proximal position the buttress tabs are positioned within the right and left first portions.

8. The reloadable cartridge assembly of claim 7 wherein when the cover is in the distal position the buttress is released and at least two left buttress tabs and at least two right buttress tabs being positioned adjacent to the at least two left tabs and at least two right tabs.

9. The reloadable cartridge assembly of claim 8 wherein when the cover is in the distal position, the at least two buttress tabs are positioned within the left and right second portions.

10. The reloadable cartridge assembly of claim 1 wherein the anvil further comprises two proximal openings, two tip openings, each with a tip cleat positioned within each tip opening; wherein the anvil buttress comprises two surface openings and a distal tab; and wherein the staple cartridge further comprises a pair of cartridge cleats.

11. The reloadable cartridge assembly of claim 10 wherein the suture is positioned, sequentially, through a first tip opening, over the top of the distal tab, through the other tip opening, wherein each end of the suture is attached to a tip cleat; and a second suture is positioned through one anvil opening, through one surface opening in the anvil buttress, back through the other surface opening in the anvil buttress, and through the second anvil opening, wherein each end of the second suture is attached to an anvil cleat.

12. A staple cartridge, comprising:
   a proximal and distal end, a top and bottom surface, a plurality of staples, and a moveable cover; and
   a cartridge buttress, positioned on the top surface of the cartridge, and releasably secured to the cartridge by positioning the cover in a proximal position;
   wherein the cover is configured to move distally to release the cartridge buttress from the staple cartridge.

13. The staple cartridge of claim 12 wherein the staple cartridge further comprises a slot wherein a section of an I-beam is positioned within the slot and a portion of the I-beam is positioned on an exterior of the staple cartridge.

14. The staple cartridge of claim 13 wherein the cover further comprises an edge, wherein the portion of the I-beam that is exterior to the cartridge interfaces with the edge to move the cover distally.

15. The staple cartridge of claim 14 wherein the buttress comprises at least two right buttress tabs and at least two left buttress tabs and wherein the cover further comprises at least two left openings and at least two right openings, where each opening comprises a first portion and a second portion, and at least two left tabs and at least two right tabs.

16. The staple cartridge of claim 15 wherein when the cover is in a proximal position, the cartridge buttress is releasably secured to the buttress due to the at least two left buttress tabs and at least two right buttress tabs being positioned between the at least two left and at least two right tabs and a body of the staple cartridge.

17. A reloadable cartridge assembly, comprising:
   a staple cartridge comprising a proximal and distal end, a surface, a plurality of staples, and a left plate and a right plate, each positioned on one side surface of the staple cartridge, comprising at least two left flaps and at least two right flaps, with an interior raised projection positioned on each flap, with the interior raised projection extending toward the side surface of the staple cartridge;
   an anvil comprising a proximal and distal end, a surface and two sides;
   an I-beam configured to move through the staple cartridge and anvil;
   an anvil buttress, positioned on the surface and sides of the anvil, with a top surface facing away from the surface of the anvil and releasably secured to the anvil with at least one suture; and
   a cartridge buttress, positioned on the surface and sides of the cartridge, comprising at least two right side tabs and at least two left side tab, and releasably secured to the cartridge by positioning each of the at least two right side tabs and the at least two left side tabs between a flap and the staple cartridge;
   wherein the I-beam is configured to move the interior raised projections and the flap in a direction away from the cartridge body to release the cartridge buttress from the staple cartridge.

18. The reloadable cartridge assembly of claim 17 further comprising, a staple driver, the staple driver being configured to push the staples out of the cartridge and toward the anvil and to move the internal raised projections in a direction away from the cartridge in response to the I-beam being moved distally.

19. The reloadable cartridge assembly of claim 18 wherein the plate further comprises exterior raised projections positioned on the flaps, wherein the cartridge buttress tabs are positioned over the exterior raised projections and between the flap and the cartridge body.

20. The reloadable cartridge assembly of claim 17, wherein the at least two right tabs and at least two left tabs comprise a first and second right tab and a first and a second left tab, wherein the at least two buttress left tabs and at least two right tabs comprise a first and second left and right tabs, wherein the first left buttress tab is positioned between the first left flap and the cartridge body, the second left buttress tab is positioned between the second left flap and the cartridge body, the first right buttress tab is positioned between the first right flap and the cartridge body, the second right buttress tab is positioned between the second right flap and the cartridge body.

* * * * *